United States Patent
Eastham

(10) Patent No.: US 7,772,419 B2
(45) Date of Patent: Aug. 10, 2010

(54) CARBONYLATION OF ESTER

(75) Inventor: Graham Eastham, Co Durham (GB)

(73) Assignee: Lucite International UK Ltd., Hampshire (GB)

( * ) Notice: Subject to any disclaimer, the term of this patent is extended or adjusted under 35 U.S.C. 154(b) by 149 days.

(21) Appl. No.: 11/597,787

(22) PCT Filed: May 18, 2005

(86) PCT No.: PCT/GB2005/001911

§ 371 (c)(1),
(2), (4) Date: Nov. 15, 2007

(87) PCT Pub. No.: WO2005/118519

PCT Pub. Date: Dec. 15, 2005

(65) Prior Publication Data

US 2008/0086015 A1   Apr. 10, 2008

(30) Foreign Application Priority Data

May 28, 2004  (GB)  ................................. 0411951.7

(51) Int. Cl.
C07C 69/66 (2006.01)
C07C 51/14 (2006.01)
C07C 59/08 (2006.01)

(52) U.S. Cl. ..................... 560/179; 562/522; 562/589

(58) Field of Classification Search .................. None
See application file for complete search history.

(56) References Cited

U.S. PATENT DOCUMENTS

| | | |
|---|---|---|
| 4,377,708 A | 3/1983 | Morris |
| 4,500,727 A | 2/1985 | Kitamura et al. |
| 4,504,684 A | 3/1985 | Fox et al. |
| 4,517,061 A | 5/1985 | Fauvarque |
| 4,786,443 A | 11/1988 | Drent et al. |
| 4,900,413 A | 2/1990 | Sakakura et al. |
| 4,960,926 A | 10/1990 | Drent |
| 4,960,949 A | 10/1990 | Devon et al. |
| 5,028,576 A | 7/1991 | Drent et al. |
| 5,099,062 A | 3/1992 | Drent et al. |
| 5,103,043 A | 4/1992 | Drent et al. |
| 5,149,868 A | 9/1992 | Drent |
| 5,158,921 A | 10/1992 | Drent et al. |
| 5,166,116 A | 11/1992 | Drent et al. |
| 5,177,253 A | 1/1993 | Drent et al. |
| 5,179,225 A | 1/1993 | Drent et al. |
| 5,189,003 A | 2/1993 | Klusener et al. |
| 5,210,280 A | 5/1993 | Drent |
| 5,245,098 A | 9/1993 | Summers et al. |
| 5,246,558 A | 9/1993 | Chevigne et al. |
| 5,258,546 A | 11/1993 | Klusener et al. |
| 5,436,356 A | 7/1995 | Drent et al. |
| 5,563,308 A | 10/1996 | Spindler et al. |
| 5,710,344 A | 1/1998 | Breikss et al. |
| 5,760,264 A | 6/1998 | Brieden |
| 5,783,715 A | 7/1998 | Pugin |
| 5,962,732 A | 10/1999 | Burke |
| 6,015,919 A | 1/2000 | Pugin |
| 6,156,934 A | 12/2000 | Suykerbuyk et al. |
| 6,169,192 B1 | 1/2001 | Pugin et al. |
| 6,191,284 B1 | 2/2001 | Knochel et al. |
| 6,258,979 B1 | 7/2001 | Kagan et al. |
| 6,284,919 B1 | 9/2001 | Pearson et al. |
| 6,284,925 B1 | 9/2001 | Knochel et al. |
| 6,307,065 B1 | 10/2001 | Tjaden et al. |
| 6,335,471 B1 | 1/2002 | Eastham et al. |
| 6,348,621 B1 | 2/2002 | Wang et al. |
| 6,391,818 B1 | 5/2002 | Bonsel et al. |
| 6,462,095 B1 | 10/2002 | Bonsel et al. |

(Continued)

FOREIGN PATENT DOCUMENTS

DE   19745904 A1   4/1999

(Continued)

OTHER PUBLICATIONS

Related U.S. Appl. No. 10/524,023, filed Nov. 17, 2005, Eastham et al.

(Continued)

*Primary Examiner*—Paul A Zucker
(74) *Attorney, Agent, or Firm*—Venable LLP; Keith G. Haddaway; Michael E. Nelson

(57) ABSTRACT

A vinyl ester alkoxycarbonylation process comprising reacting a vinyl ester with carbon monoxide in the presence of an alkanol and a catalyst system. The catalyst system used is obtainable by combining:
  a) a metal of Group VIII B or a compound thereof, and
  b) a bidentate ligand of general formula (I)

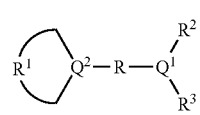

(I)

R is a covalent bridging group; $R^1$ together with $Q^2$ to which form an optionally substituted 2-$Q^2$-tricyclo[3.3.1.1{3,7}] decyl group or derivative thereof (2-PA); $R^2$ and $R^3$ independently represent univalent radicals up to 20 atoms or jointly form a bivalent radical of up to 20 atoms; and $Q^1$ and Q2 each independently represent phosphorous, arsenic or antimony. The process is carried out for the production of a 3-hydroxy propanoate ester or acid of formula (II)

$$CH_2(OH)CH_2C(O)OR^{28} \quad (II).$$

or for the production of a lactate ester or acid of formula III.

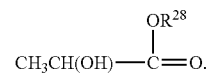

(III)

18 Claims, No Drawings

U.S. PATENT DOCUMENTS

| | | |
|---|---|---|
| 6,476,255 B1 | 11/2002 | Hadden et al. |
| 6,521,769 B1 | 2/2003 | Zhang |
| 6,706,912 B2 | 3/2004 | Drent et al. |
| 6,723,882 B2 | 4/2004 | Slany et al. |
| 6,743,911 B2 | 6/2004 | Drent et al. |
| 6,753,450 B2 | 6/2004 | Ahlers et al. |
| 6,916,954 B2 | 7/2005 | Schafer et al. |
| 6,982,357 B2 | 1/2006 | Crabtree et al. |
| 6,984,668 B1 | 1/2006 | Eastham et al. |
| 7,026,473 B2 | 4/2006 | Drent et al. |
| 7,148,176 B2 | 12/2006 | Beller et al. |
| 7,265,240 B2 | 9/2007 | Eastham et al. |
| 7,371,705 B2 | 5/2008 | Eastham et al. |
| 2001/0051745 A1 | 12/2001 | Pearson et al. |
| 2002/0045748 A1 | 4/2002 | Drent et al. |
| 2003/0191339 A1 | 10/2003 | Schfer et al. |
| 2004/0162440 A1 | 8/2004 | Bunel et al. |
| 2005/0090694 A1 | 4/2005 | Drent et al. |
| 2006/0106259 A1 | 5/2006 | Eastham et al. |
| 2006/0122435 A1 | 6/2006 | Eastham et al. |
| 2006/0128985 A1 | 6/2006 | Eastham et al. |
| 2006/0252935 A1 | 11/2006 | Eastham et al. |
| 2008/0086015 A1 | 4/2008 | Eastham |

FOREIGN PATENT DOCUMENTS

| | | |
|---|---|---|
| DE | 19754304 A1 | 6/1999 |
| DE | 10023470 A1 | 11/2001 |
| DE | 10037961 A1 | 2/2002 |
| EP | 0 055 875 | 7/1982 |
| EP | 0055875 A1 | 7/1982 |
| EP | 0 106 379 | 4/1984 |
| EP | 0106379 A1 | 4/1984 |
| EP | 0 144 118 | 6/1985 |
| EP | 0 227 160 | 1/1987 |
| EP | 0227160 A2 | 7/1987 |
| EP | 0 235 864 | 9/1987 |
| EP | 0235864 A1 | 9/1987 |
| EP | 0274795 | 7/1988 |
| EP | 0274795 A2 | 7/1988 |
| EP | 0282142 | 9/1988 |
| EP | 0282142 A1 | 9/1988 |
| EP | 0305089 A1 | 3/1989 |
| EP | 0375573 A1 | 6/1990 |
| EP | 0386833 | 9/1990 |
| EP | 0386833 A1 | 9/1990 |
| EP | 0441447 | 8/1991 |
| EP | 0441447 A1 | 8/1991 |
| EP | 0489472 | 6/1992 |
| EP | 0489472 A2 | 6/1992 |
| EP | 0 495 348 A1 | 7/1992 |
| EP | 0 495 548 | 7/1992 |
| EP | 0495347 | 7/1992 |
| EP | 0495547 A2 | 7/1992 |
| EP | 0495548 A2 | 7/1992 |
| EP | 0499329 | 8/1992 |
| EP | 0499329 A1 | 8/1992 |
| EP | 0577205 A2 | 1/1994 |
| EP | 0683764 A1 | 11/1995 |
| EP | 0728733 A1 | 8/1996 |
| EP | 0879642 A2 | 11/1998 |
| EP | 1330309 A1 | 7/2003 |
| FR | 2034147 A5 | 12/1970 |
| GB | 2006208 A | 5/1979 |
| JP | 08134218 A | 5/1996 |
| WO | WO 96/19434 | 6/1996 |
| WO | WO-96/19434 A1 | 6/1996 |
| WO | WO-97/08124 A1 | 3/1997 |
| WO | WO-98/41495 A1 | 9/1998 |
| WO | WO 98/42717 | 10/1998 |
| WO | WO-98/42717 A1 | 10/1998 |
| WO | WO-98/45040 A1 | 10/1998 |
| WO | WO-99/47528 A1 | 9/1999 |
| WO | WO-00/56695 A1 | 9/2000 |
| WO | WO-01/10551 A1 | 2/2001 |
| WO | WO-01/28972 A1 | 4/2001 |
| WO | WO-01/65583 A1 | 9/2001 |
| WO | WO-01/68583 A2 | 9/2001 |
| WO | WO-0168583 | 9/2001 |
| WO | WO-0170659 | 9/2001 |
| WO | WO-01/72697 A2 | 10/2001 |
| WO | WO-01/85662 A2 | 11/2001 |
| WO | WO 02/12161 | 2/2002 |
| WO | WO-03/040159 A2 | 5/2003 |
| WO | WO-03/070370 A1 | 8/2003 |
| WO | WO-03070370 | 8/2003 |
| WO | WO 2004/014552 | 2/2004 |
| WO | WO-2004/014552 A1 | 2/2004 |
| WO | WO-2004/014834 A1 | 2/2004 |
| WO | WO 2004/024322 | 3/2004 |
| WO | WO-2004/024322 A2 | 3/2004 |
| WO | WO-2004/050599 A1 | 6/2004 |
| WO | WO-2004/103948 A1 | 12/2004 |
| WO | WO-2005/003070 A1 | 1/2005 |
| WO | WO-2005/079981 A1 | 9/2005 |
| WO | WO-2005/082830 A1 | 9/2005 |
| WO | WO-2005/118519 A1 | 12/2005 |
| WO | WO-2006/062467 A1 | 6/2006 |
| WO | WO-2006/084892 A2 | 8/2006 |
| WO | WO-2007/119079 A1 | 10/2007 |

OTHER PUBLICATIONS

Lide et al., Handbook of Chem and Phys., 76$^{th}$ Ed., CRC Press, 1995, ps. 8-141-6-155 to 6-17; 15-16 to 15-25.

Pugh, R. I. et al. "Tandem isomerisation-carbonylation catalysis: highly active palladium(II) catalysts for the selective methoxycarbonylation of internal alkenes to linear esters", Chemical Communications—CHEMCOM, Royal Society of Chemistry, GB, No. 16, (Aug. 21, 2001), pp. 1476-1477.

Kirk Othmer Encyclopaedia of Chemical Terminology, vol. 9, 4th Ed., p. 783, Hydrolysis of Organic Esters, pp. 783-85 and 87, John Wiley & Sons, Jan. 1994.

Masters, Christopher, "Homogeneous Transition Metal Catalysis," p. 4-21, Chapman and Hall, Feb. 1981.

Wang et al., "Polymer-Bound Bidentate-Phosphine-Palladium Complex as a Catalyst in the Heck Arylation", J. Org. Chem, vol. 59, No. 18, 1994, pp. 5358-5364.

Hofmann et al., "BIS(Di-T-Butylphosphino)Methane Complexes of Rhodium: Homogeneous Alkyne Hydrosilylation by Catalyst-Dependent Alkyne Insertion Into Rh-Si or Rh-H Bonds. Molecular Structures of the Dimer [(dtbpm) RHcL]$_2$ and of the Silyl Complex (dtbpm) Rh[Si(OEt)$_3$](PMe$_3$)", Journal of Organometallic Chemistry, vol. 490, 1995, pp. 51-70.

Lindner et al., "Catalytic Activity of Cationic Diphospalladium (II) Complexes in the Alkene/CO Copolymerization in Organic Solvents and Water in Dependence on the Length of the Alkyl Chain at the Phosphine Ligands", Journal of Organometallic Chemistry, vol. 602, 2000, pp. 173-187.

Richmond et al., "Preparation of New Catalysts by the Immobilization of Palladium(II) Species onto Silica: An Investigation of Their Catalytic Activity for the Cyclization of Aminoalkynes", J. Am Chem. Soc., vol. 123, 2001, pp. 10521-10525.

Tamao et al., "Alkyl Group Isomerization in the Cross-Coupling Reaction of Secondary Alkyl Grignard Reagents with Organic Halides in the Presence of Nickel-Phosphine Complexes as Catalysts", Journal of the American Chemical Society, vol. 94, 1972, pp. 9268-9269.

Jones et al, "Rhodium-Catalyzed Activation and Functionalization of the C-C Bond of Biphenylene", Organometallics, vol. 20, 2001, pp. 5745-5750.

"Highly active [Pd(AcO)$_2$(dppp(] catalyst for the CO-C$_2$H$_4$ copolymerization in H$_2$O-CH$_3$COOH solvent [dppp = 1,3-bis (diphenylphosphino)propane]" Andrea Vavasori et al., Journal of Molecular Cat. A. Chem., vol. 204-205, 2003, pp. 295-303.

"Hydroesterification of styrene using an in situ formed Pd(OTs)$_2$(PPh$_3$)$_2$ complex catalyst", A. Seayad et al., Journal of Molecular Cat. A. Chem., vol. 151, 2000, pp. 47-59.

"Carbon monoxide-ethylene copolymerization catalyzed by a Pd(AcO)$_2$/dpppTsOH[1] system: the promoting effect of water and of the acid", Journal of Molecular Cat. A. Chem., vol. 110, 1996, pp. 13-23.

Clegg, W. et al: "Highly active and selective catalysts for the production of methl propanoate via the methoxycarbonylation of ethene" Chem. Commun., 1999, pp. 1877-1878.

Knight et al: "Remarkable Differences in Catalyst Activity and Selectivity fo rthe production of Methyl Propanoate versus CO-Ethylene Copolymer by a Series of palladium Complexes of Related C4-Bridged Diphosphines" Organometallics 2000, 19 4957-4967.

Adam J. Rucklidge et al.: "Methoxycarbonylation f vinyl acetate catalysed by palladium comlexes of bis )ditertiarybutylphosphinomethyl) benzene and related ligands" Chem. Commun., 2005, pp. 1176-1178.

Brunkan et al. "Effect of chiral cavities associated with molecularly imprinted platinum centers on the selectivity of ligand-exchange reactions at platinum", Journal of American Chemical Society, No. 22, pp. 6217-6225, (2000).

Brunkan et al. "Unorthodox C,O binding mode of Me$_2$BINOL in Pt(II) complexes", Journal of American Chemical Society, No. 120, pp. 11002-11003, (1998).

Andrews et al. "Regioselective complexation of unprotected carbohydrates by Platinum(II); Synthesis, structure, complexation equilibria, and hydrogen-bonding in carbonate-derived bis(phosphine)platinum(II) diolate and alditolate complexes", Journal of American Chemical Society, No. 116, pp. 5730-5740, (1994).

Hartwig, et al. "Structure and reactions of oxametallacyclobutanes and oxametallacyclobutenes of ruthenium", Organometallics, vol. 10, No. 9, pp. 3344-3362 (1991).

Konno et al. "Preparation and spectroscopic characteristics of geometrical isomers of bis[1,2-bis(dimethylphosphino)ethane]cobalt(III) complexes with thiolate ligands", The Chemical Society of Japan, No. 62, pp. 3475-3478, (1989).

Cecconi et al. "Palladium complexes with the tripodal phosphine tris(2-diphenylphosphinoethyl)amine. Synthesis and structure of trigonal, tetrahedral, trigonal bipyramidal, and square planar complexes", J. Chem. Soc. Dalton Trans., issue 1, pp. xvii-xx. (1989).

Miskowski et al. "Preparation and spectroscopic properties of Cobalt(III) complexes containing phosphine ligands. The electronic structural description of side-bonded dioxygen", Journal of American Chemical Society, vol. 98, No. 9, pp. 2477-2483, (1976).

Hayward et al. "Some reactions of peroxobis (triphenylphosphine)platinum(II) and analogs with carbon dioxide, carbon disulfide, and other unsaturated molecules", Journal of American Chemical Society, vol. 92, issue 20, pp. 5873-5878, (1970).

Osman, Serindag "Synthesis of some platinum(II) diphosphine complexes of the type [PtX2(P-P)] (X2 = CO3; X = CH3COO, CF3COO, NCO)", Synth. React. Inorg. Met.-Org. Chem., vol. 27. No. 1, pp. 69-76, (1997).

Andrews et al. "Syntheses, spectra and structures of (diphosphine)platinum(II) carbonate complexes" Inorganic Chemistry, No. 35, pp. 5478-5483, (1996).

Latif et al. "Square planar platinum(II) complexes, crystal structures of cis-bis(triphenylphosphine) hydro(triphenylstannyl) platinum(II) and cis-bis(triphenylphosphine) hydro(triphenylsilyl) platinum(II)", Journal of Organometallic Chemistry, No. 474, pp. 217-221, (1994).

Becker et al. "Synthesis and characterization of chiral diphosphine platinum(II) VANOL and VAPOL complexes", Organometallics, No. 22, pp. 3245-3249, (2003).

Becker et al. "Imprinting chiral information into rigidified dendrimers", Organometallics, No. 22, pp. 4984-4998, (2003).

Peng et al. "Chiral rodlike platinum complexes, double helical chains and potential asymmetric hydrogenation ligand based on "linear" building blocks: 1,8,9,16-tetrahydroxytetraphenylene and 1,8,9,16-tetrakis(diphenylphosphino)tetraphenylene" Journal of American Chemical Society, No. 127, pp. 9603-9611, (2005).

Wen et al. "Synthesis, resolution, and applications of 1,16-dihydroxytetraphenylene as a novel building block in molecular recognition and assembly", Journal of Organic Chemistry, No. 68, pp. 8918-8931, (2003).

Mikami et al. "Molecular design of DABNTf as a highly efficient resolving reagent for racemic Pd complex with *tropos* biphenylphosphine (BIPHEP) ligand: circular dichroism (CD) spectra of enantiopure BIPHEP-Pd complex", Chirality, No. 15, pp. 105-107, (2003).

Tudor et al. "Diastereoisomer interconversion in chiral BiphepPtX$_2$ complexes", Organometallics, No. 19, pp. 4376-4384, (2000).

Bellabarba et al., "Synthesis, X-ray characterization and reactions of a trigonal planar palladium()) carbonyl complex", Chemical Communications, No. 15, pp. 1916-1917, (2003).

Clegg et al., "Synthesis and reactivity of palladium hydrido-solvento complexes, including a key intermediate in the catalytic methoxycarbonylation of ethane to methypropanoate", Journal of the Chemical Society, Dalton Transactions, No. 17, pp. 3300-3308 (2002).

Clegg et al., "Characterisation and dynamics of [Pd(L-L)H(solv)]+, [Pd(L-L(CH2CH3)]+ and [Pd(L-L)(C(0)Et)(THF)]+ (L-L = 1,2-(CH2PBut2)2C6H4): key intermediates in the catalytic methoxycarbonylation of ethane to methylpropanoate", Organometallics, vol. 21, No. 9, pp. 1832-1840 (2002).

Edelbach et al., "Catalytic hydrogenolysis of biphenylene with platinum, palladium, and nickelphosphine complexes", Organometallics, vol. 17, No. 22, pp. 4784-4794 (1998).

Kim et al., "Synthesis and theoretical study of palladium (II) complexes with aminophosphines as 7-membered chelate rings", Bulletin of the Korean Chemical Society, vol. 18, No. 11, pp. 1162-1166 (1997).

Reddy et al., "Unexpected cross-metathesis between Si-C and Si-Si bonds", Chemical Communications, No. 16, pp. 1865-1866 (1996).

Uchimaru et al., "Ring-opening polymerization of 1,1,2,2-tetramethyl-1,2-disilacyclopentane via palladium complex-catalysed Si-Si bond metathesis", Chemistry Letters, No. 2, p. 164 (1995).

Portnoy et al., "Reactions of electron-rich arylpalladium complexes with olefins. Origin of the chelate effect in vinylation catalysis", Organometallics, vol. 13, No. 9, pp. 3465-3479 (1994).

Wurst et al., "Synthesis and structure of the platinum (0) compounds [(dipb)Pt]2(COD) and (dipb)3Pt2 and of the cluster Hg6[Pt(dipb)]4 (dipb = (iPr)2P(CH2)4P(i-Pr)2)", Zeitschrift Für Anorganische Und Allgemeine Chemie, vol. 395, pp. 239-250 (1991).

Tanaka et al., "Synthesis of ketones via carbonylation of organic halides. II. Palladium-catalysed carbonylation of organic halides with terminal acetylenes in the presence of amines. Novel acetylenic ketone synthesis", Nippon Kagaku Kaishi, No. 3, pp. 537-546 (1985).

Molander et al., "Synthesis and application of chiral cyclopropane-based ligands in palladium-catalyzed allylic alkylation", Journal of Organic Chemistry, vol. 69, No. 23, pp. 8062-8069 (2004).

Brauer et al., "Reactions of coordinated ligands. XIV. Synthesis of a tetradentate phosphorus macrocycle in a palladium (II) template", Chemische Berichte, vol. 119, No. 1, pp. 349-365 (1986).

Dias et al., "Synthesis and characterization of .eta.5-monocyclopentadienyl (p-nitrobenzonitrile)ruthenium(II) salts: second harmonic generation powder efficiencies", Journal of Organometallic Chemistry, vol. 475, No. 1-2, pp. 241-245 (1994).

Cullen et al, "Structure of the Hydrogenation Catalyst [(PP)Rh(NBD)]ClO4, (PP) = ( 5-[(CH3)3C]2PC5H4)2Fe, and Some Comparative Rate Studies," Organometallics, vol. 2, pp. 714-719, 1983.

Abbenhuis et al., "Successful Application of a "Forgotten" Phosphine in Asymmetric Catalysis: A 9-Phosphabicyclo[3.3.1]non-9-yl Ferrocene Derivative as a Chiral Ligand," Organometallics, vol. 14, pp. 759-766, 1995.

"Handbook of Chemistry and Physics", 76th Edition, edited by David R Lide et al—CRC Press, 1995; pp. 6-156 to 6-177; 8-141 and 15-16 to 15-25.

"Homogeneous Transition Metal Catalysis—A Gentle Art", C Masters, Chapman & Hall, 1981, title page, contents page and pp. 4-21.

Olah, George A., et al., "AICI3-Catalyzed Dichlorophosphorylation of Saturated Hydrocarbons with PCI3 in Methylene Chloride Solution," J. Org. Chem., 1990, 55, 1224-1227.

Wei-Yong Yu, et al., "Preparation of Polymer-Protected Pt/Co Bimetallic Colloid and its Catalytic Properties in Selective Hydrogenation of Cinnamaldehyde to Cinnamyl Alcohol," Polymers for Advanced Technologies, GB, John Wiley and Sons, Chichester, Aug. 1, 1996, 719-722, vol. 7, No. 8.

Tolman, "Phosphorous Ligand Exchange Equilibria on Zerovalent Nickel. A Dominant Role for Steric Effects," Journal of the American Chemical Society, vol. 92, No. 10, pp. 2956-2965, 1970.

Tolman, "Steric Effects of Phosphorous Ligands in Organometallic Chemistry and Homogeneous Catalysis," Chemical Reviews, vol. 77, No. 3, pp. 313-348, 1977.

Grimmer, et al., "Zirconium bis-cyclopentadienyl compounds: An investigation into the influence of substituent effects on the ethene polymerisation behaviour of (CpR)2ZrCI2/MAO catalysts," Journal of Molecular Catalysis A: Chemical, vol. 188, No. 1-2, pp. 105-113, 2002.

Machine Translation of JP 08-134218, May 28, 1996.

Office Action for U.S. Appl. No. 10/561,912, issued by the USPTO on Aug. 25, 2008.

Office Action for U.S. Appl. No. 10/561,912, issued by the USPTO on Sep. 2, 2009.

Office Action for U.S. Appl. No. 10/561,912, issued by the USPTO on Jan. 14, 2008.

Office Action for U.S. Appl. No. 10/561,912, issued by the USPTO on Feb. 11, 2009.

Office Action for U.S. Appl. No. 10/536,801, issued by the USPTO on Apr. 8, 2008.

Office Action for U.S. Appl. No. 10/536,801, issued by the USPTO on Jan. 7, 2010.

Office Action for U.S. Appl. No. 10/536,801, issued by the USPTO on Jun. 17, 2009.

CARBONYLATION OF ESTER

The present invention relates to the alkoxycarbonylation of an unsaturated ester, specifically vinyl acetate and, in particular but not exclusively, the use of the alkoxycarbonylation to provide a first step in the production of methyl lactate and 3-hydroxymethyl propanoate.

Currently methyl lactate is produced by esterification of lactic acid, which is produced either by synthetic methods or fermentation.

The main synthetic routes are based on the reactions of acetaldehyde. In one method, acetaldehyde is reacted with hydrogen cyanide to produce a lactonitrile, which is then hydrolysed. Alternatively, acetaldehyde can be reacted with carbon monoxide and water in the presence of a nickel (II) iodide or sulphuric acid catalyst. Synthetic routes produce racemic mixtures of lactic acid, and so racemic mixtures of methyl lactate result. In recent years, improvements in fermentation methods have made this a preferred route to lactic acid and its derivatives. Optically pure lactic acid can be produced by the fermentation of sugars with carefully chosen bacteria. Lactobacilli tend to be heat resistant, so fermentation at temperatures of around 50° C. suppresses secondary reactions. The procedure is slow, and requires careful monitoring of pH, temperature and oxygen levels, but by selecting an appropriate bacteria culture, optically pure lactic acid, of both R and S forms can be produced.

Methyl lactate is used as a high boiling point solvent, and is present in a variety of materials such as detergents, degreasing agents, cosmetics and food flavourings. It is biodegradable, and so environmentally friendly.

A route to 1,3-propanediol would be industrially favourable, as there is currently not a route to the diol that is commercially viable. In the 1980s, Davy Process Technology found a route to 1,4-butanediol, by forming diethyl maleate from butanes over a solid acid catalyst, and then dehydrogenating it to the diol. 1,4-butanediol is now widely used as a polymer component and also in fibre production and as a high boiling solvent. Polyhydric alcohols are often used in reactions with isocyanates to produce urethanes, and in reactions with acids and acid anhydrides to produce (poly) esters. 1,3-propanediol is thought to have uses as a polymer component and as a high boiling point solvent.

The carbonylation of ethylenically unsaturated compounds using carbon monoxide in the presence of an alcohol or water and a catalyst system comprising a group VIB OR VIIIB metal, example, palladium, and a phosphine ligand, example an alkyl phosphine, cycloalkyl) phosphine, aryl phosphine, pyridyl phosphine or bidentate phosphine, has been described in numerous European patents and patent applications, example EP-A-0055875, EP-A-04489472, EP-A-0106379, EP-A-0235864, EP-A-0274795, EP-A-0499329, EP-A-0386833, EP-A-0441447, EP-A-0489472, EP-A-0282142, EP-A-0227160, EP-A-0495547 and EP-A-0495548. In particular, EP-A-0227160, EP-A-0495547 and EP-A-0495548 disclose that bidentate phosphine ligands provide catalyst systems which enable high reaction rates to be achieved.

WO96/19434 discloses that a particular group of bidentate phosphine compounds can provide remarkably stable catalysts which require little or no replenishment; that use of such bidentate catalysts leads to reaction rates which are significantly higher than those previously disclosed; that little or no impurities are produced at high conversions.

WO 01/68583 discloses rates for the same process used for higher alkenes when in the presence of an externally added aprotic solvent.

EP0495548B1 gives an example of vinyl acetate carbonylation employing the C3 bridged phosphine 1,3bis(di-tert-butylphosphino) propane. The rates quoted are 200 moles product per mole of Pd per hour and the result is the production of 1 and 2-acetoxy methyl propanoate in a ratio of 40:60 (linear:branched).

WO 98/42717 discloses a modification to the bidentate phosphines used in EP0495548 wherein one or both phosphorous atoms are incorporated into an optionally substituted 2-phospha-tricyclo[3.3.1.1{3,7}]decyl group or a derivative thereof in which one or more of the carbon atoms are replaced by heteroatoms ("2-PA" group). The examples include a number of alkoxycarbonylations of ethene, propene and some higher terminal and internal olefins. In addition, hydroformylation of vinyl acetate giving a branched:linear product ratio of 10:1 is also disclosed. Notably, no alkoxycarbonylation of vinyl acetate is disclosed.

WO 03/070370 extends the teaching of WO 98/42717 to bidentate phosphines having 1, 2 substituted aryl bridges of the type disclosed in WO96/19434. The suitable olefin substrates disclosed include several types having various substituents. Notably, vinyl esters are not mentioned either generally or specifically.

Vinyl esters are known to hydrolyse easily into the corresponding acid or aldehyde. Accordingly, exposure of vinyl ester to acid should be avoided. Alkoxycarbonylation reactions with bidentate phosphines may proceed in the presence of Group VIB OR VIIIB metals but such metals are utilised in the presence of a source of anions derived from acids having a pKa of less than 4. Accordingly, alkoxycarbonylation may be deemed unsuitable for carbonylation of vinyl ester.

According to a first aspect of the present invention there is provided a process for the alkoxycarbonylation of a vinyl ester comprising reacting a vinyl ester with carbon monoxide in the presence of an alkanol and of a catalyst system, the catalyst system obtainable by combining:

(a) a metal of Group VIII B or a compound thereof: and (b) a bidentate ligand of general formula (I)

wherein:

R is a covalent bridging group;

$R^1$ together with $Q^2$ to which it is attached form an optionally substituted 2-$Q^2$-tricyclo[3.3.1.1{3,7}]decyl group or derivative thereof (2-PA);

R2 and R3 independently represent univalent radicals upto 20 atoms or jointly form a bivalent radical of up to 20 atoms;

$Q^1$ and $Q^2$ each independently represent phosphorous, arsenic or antimony.

Preferably, $Q^2$ is phospha and preferably, $Q^1$ is phospha.

Preferably, $R^2$ represents $CR^4(R^5)(R^6)$, congressyl or adamantyl, $R^3$ represents $CR^7(R^8)(R^9)$, congressyl or adamantyl, or $R^2$ and $R^3$ together with $Q^1$ to which they are attached form an optionally substituted 2-$Q^1$-tricyclo[3.3.1.1{3,7}]decyl group or derivative thereof.

Preferably, the bidentate ligand is a bidentate phosphine, arsine or stibine ligand, preferably, a phosphine ligand.

The adamantyl group may optionally comprise, besides hydrogen atoms, one or more substituents selected from lower alkyl, $-OR^{19}$, $-OC(O)R^{20}$, halo, nitro, $-C(O)R^{21}$, $-C(O)OR^{22}$, cyano, aryl, $-N(R^{23})R^{24}$, $-C(O)N(R^{25})R^{26}$, $-C(S)(R^{27})R^{28}$, $-CF_3$, $-P(R^{56})R^{57}$, $-PO(R^{58})(R^{59})$, $-PO_3H_2$, $-PO(OR^{60})(OR^{61})$, or $-SO_3R^{62}$, wherein $R^{19}$, $R^{20}$, $R^{21}$, $R^{22}$, $R^{23}$, $R^{24}$, $R^{25}$, $R^{26}$, $R^{27}$, $R^{28}$, lower alkyl, cyano and aryl are as defined herein and $R^{56}$ to $R^{62}$ each independently represent hydrogen, lower alkyl, aryl or Het.

Suitably, when the adamantyl group is substituted with one or more substituents as defined above, highly preferred substituents include unsubstituted $C_1$ to $C_8$ alkyl, $-OR^{19}$, $-OC(O)R^{20}$, phenyl, $-C(O)OR^{22}$, fluoro, $-SO_3H$, $-N(R^{23})R^{24}$, $-P(R^{56})R^{57}$, $-C(O)N(R^{25})R^{26}$ and $-PO(R^{58})(R^{59})$, $-CF_3$, wherein $R^{19}$ represents hydrogen, unsubstituted $C_1$-$C_8$ alkyl or phenyl, $R^{20}$, $R^{22}$, $R^{23}$, $R^{24}$, $R^{25}$, $R^{26}$ each independently represent hydrogen or unsubstituted $C_1$-$C_8$ alkyl, $R^{56}$ to $R^{59}$ each independently represent unsubstituted $C_1$-$C_8$ alkyl or phenyl.

Suitably, the adamantyl group may comprise, besides hydrogen atoms, up to 10 substituents as defined above, preferably up to 5 substituents as defined above, more preferably up to 3 substituents as defined above. Suitably, when the adamantyl group comprises, besides hydrogen atoms, one or more substituents as defined herein, preferably each substituent is identical. Preferred substituents are unsubstituted $C_1$-$C_8$ alkyl and trifluoromethyl, particularly unsubstituted $C_1$-$C_8$ alkyl such as methyl. A highly preferred adamantyl group comprises hydrogen atoms only i.e. the adamantyl group is not substituted.

Preferably, when more than one adamantyl group is present in a compound of formula I, each adamantyl group is identical.

The 2-$Q^2$(or $Q^1$)-tricyclo[3.3.1.1.{3,7}]decyl group (referred to hereinafter as a 2-meta-adamantyl group for convenience wherein 2-meta-adamantyl is a reference to 2-arsa-adamantyl and/or 2-stiba-adamantyl and/or 2-phospha-adamantyl, preferably, 2-phospha-adamantyl) may optionally comprise, beside hydrogen atoms, one or more substituents. Suitable substituents include those substituents as defined herein in respect of the adamantyl group. Highly preferred substituents include lower alkyl, particularly unsubstituted $C_1$-$C_8$ alkyl, especially methyl, trifluoromethyl, $-OR^{19}$ wherein $R^{19}$ is as defined herein particularly unsubstituted $C_1$-$C_8$ alkyl or aryl, and 4-dodecylphenyl. When the 2-meta-adamantyl group includes more than one substituent, preferably each substituent is identical.

Preferably, the 2-meta-adamantyl group is substituted on one or more of the 1, 3, 5 or 7 positions with a substituent as defined herein. More preferably, the 2-meta-adamantyl group is substituted on each of the 1, 3 and 5 positions. Suitably, such an arrangement means the Q atom of the 2-meta-adamantyl group is bonded to carbon atoms in the adamantyl skeleton having no hydrogen atoms. Most preferably, the 2-meta-adamantyl group is substituted on each of the 1, 3, 5 and 7 positions. When the 2-meta-adamantyl group includes more than 1 substituent preferably each substituent is identical. Especially preferred substituents are unsubstituted $C_1$-$C_8$ alkyl and trifluoromethyl, particularly unsubstituted $C_1$-$C_8$ alkyl such as methyl.

Preferably, 2-meta-adamantyl represents unsubstituted 2-meta-adamantyl or 2-meta-adamantyl substituted with one or more unsubstituted $C_1$-$C_8$ alkyl substituents, or a combination thereof.

Preferably, the 2-meta-adamantyl group includes additional heteroatoms, other than the 2-Q atom, in the 2-meta-adamantyl skeleton. Suitable additional heteroatoms include oxygen and sulphur atoms, especially oxygen atoms. More preferably, the 2-meta-adamantyl group includes one or more additional heteroatoms in the 6, 9 and 10 positions. Even more preferably, the 2-meta-adamantyl group includes an additional heteroatom in each of the 6, 9 and 10 positions. Most preferably, when the 2-meta-adamantyl group includes two or more additional heteroatoms in the 2-meta-adamantyl skeleton, each of the additional heteroatoms are identical. An especially preferred 2-meta-adamantyl group, which may optionally be substituted with one or more substituents as defined herein, includes an oxygen atom in each of the 6, 9 and 10 positions of the 2-meta-adamantyl skeleton.

Preferably, the 2-meta-adamantyl includes one or more oxygen atoms in the 2-meta-adamantyl skeleton.

Highly preferred 2-meta-adamantyl groups as defined herein include 2-phospha-1,3,5,7-tetramethyl-6,9,10-trioxadamantyl group, 2-phospha-1,3,5-trimethyl-6,9,10-trioxadamantyl group, 2-phospha-1,3,5,7-tetra(trifluoromethyl)-6,9,10-trioxadamantyl group, and 2-phospha-1,3,5-tri(trifluoromethyl)-6,9,10-trioxadamantyl group. Most preferably, the 2-phospha-adamantyl is selected from 2-phospha-1,3,5,7-tetramethyl-6,9,10-trioxadamantyl group or 2-phospa-1,3,5,-trimethyl-6,9,10-trioxadamantyl group.

Preferably, when more than one 2-meta-adamantyl group is present in a compound of formula I, each 2-meta-adamantyl group is identical.

The 2-meta-adamantyl group may be prepared by methods well known to those skilled in the art. Suitably, certain 2-phospha-adamantyl compounds are obtainable from Cytec Canada Inc of 901 Garner Road, Niagara Falls, Ontario, Canada L2E 6T4. Likewise corresponding 2-meta-adamantyl compounds of formula I etc may be obtained from the same supplier or prepared by analogous methods.

Suitable Group VIIIB metals or a compound thereof which may be combined with a compound of formula I include cobalt, nickel, palladium, rhodium and platinum. Preferably, the Group VIIIB metal is palladium or a compound thereof. Suitable compounds of such Group VIIIB metals include salts of such metals with, or compounds comprising weakly coordinated anions derived from, nitric acid; sulphuric acid; lower alkanoic (up to $C_{12}$) acids such as acetic acid and propionic acid; sulphonic acids such as methane sulphonic acid, chlorosulphonic acid, fluorosulphonic acid, trifluoromethane sulphonic acid, benzene sulphonic acid, naphthalene sulphonic acid, toluene sulphonic acid, e.g. p-toluene sulphonic acid, t-butyl sulphonic acid, and 2-hydroxypropane sulphonic acid; sulphonated ion exchange resins; perhalic acid such as perchloric acid; halogenated carboxylic acids such as trichloroacetic acid and trifluoroacetic acid; orthophosphoric acid; phosphonic acids such as benzenephosphonic acid; and acids derived from interactions between Lewis acids and Broensted acids. Other sources which may provide suitable anions include the optionally halogenated tetraphenyl borate derivatives, e.g. perfluorotetraphenyl borate. Additionally, zero valent palladium complexes particularly those with labile ligands, e.g. triphenylphosphine or alkenes such as dibenzylideneacetone or styrene or tri(dibenzylideneacetone)dipalladium may be used.

The anion may be derived from or introduced as one or more of an acid having a pKa measured in aqueous solution at 18° C. of less than 4, more preferably, less than 3, a salt with a cation that does not interfere with the reaction, e.g. metal salts or largely organic salts such as alkyl ammonium, and a precursor, such as an ester, that can break down under reaction conditions to generate the anion in situ. Suitable acids and salts include the acids and salts, other than unsubstituted carboxylates, listed supra The quantity of anion present is not critical to the catalytic behaviour of the catalyst system. The molar ratio of anion to palladium may be from 1:1 to 500:1, preferably from 2:1 to 100:1 and particularly from 3:1 to 30:1. Where the anion is provided by an acid and salt the relative proportion of the acid and salt is not critical. However, where an anion is provided by acid or partially provided by acid the ratio of acid to group VIIIB metal is preferably, at least 1:1 mol ($H^+$)/mol ($C^{2+}$) and preferably, less than at least 5:1 mol ($H^+$)/mol ($C^{2+}$), more preferably, the ratio is at least 2:1 and preferably, less than at least 3:1; most preferably, around a 2:1 ratio is preferred. By $H^+$ is meant the amount of active acidic sites so that a mole of monobasic acid would have 1 mole of $H^+$ whereas a mole of dibasic acid would have 2 moles of $H^+$ and tribasic acids etc should be interpreted accordingly. Similarly, by $C^{2+}$ is meant moles of metal having a $2^+$ cationic charge so that for $M^+$ ions the ratio of the metal cation should be adjusted accordingly. For example, an $M^+$ cation should be taken as having 0.5 moles of $C^{2+}$ per mole of $M^+$.

Preferably, the ratio of bidentate ligand to acid is at least 1:2 mol/mol ($H^+$) and preferably, the ratio of bidentate ligand to group VIII B metal is at least 1:1 mol/mol ($C^{2+}$). Preferably, the ligand is in excess of metal mol/mol ($C^{2+}$) and preferably in excess of a ratio of 1:2 mol/mol ($H^+$) with the acid. Excess ligand is advantageous as the ligand itself may act as a base to buffer the acid levels in the reaction and prevent degradation of vinyl ester. On the other hand the presence of acid activates the reaction mix and improves the overall rate of reaction.

As mentioned, the catalyst system of the present invention may be used homogeneously or heterogeneously. Preferably, the catalyst system is used homogeneously.

Advantageously, use of the catalyst system of the present invention in the alkoxycarbonylation of vinyl esters gives predominantly linear product. This is surprising because hydroformylation of vinyl acetate using a 2-PA ligand with a propane bridge gave predominantly branched product in WO 98/42717.

Accordingly, in a second aspect of the present invention there is provided a process for the production of 3-hydroxy propanoate ester or acid of formula (II)

$$CH_2(OH)CH_2C(O)OR^{28} \tag{II}$$

comprising the steps of:

alkoxycarbonylating vinyl ester with carbon monoxide in the presence of an alkanol and a catalyst system, the catalyst system obtainable by combining:
(a) a metal of Group VIII B or a compound thereof: and
(b) a bidentate ligand of general formula (I) in accordance with the first aspect as defined herein wherein $R^{28}$ is selected from H, or a $C_1$-$C_{30}$ alkyl or aryl moiety which may be substituted or unsubstituted and either branched or linear and carrying out a treatment step on the said linear (n) product 1-acetoxy $CH_2.CH_2C(O)OR^{28}$ to produce the 3-hydroxy propanoate ester or acid of formula (II).

The linear (n) and branched (iso) products of the alkoxycarbonylation may be separated either before or after the treatment step. Preferably, the said products are separated from the reaction products by distillation.

According to a third aspect of the present invention there is provided the use of the catalyst system as defined in any of the $1^{st}$ or $2^{nd}$ aspects of the present invention for the production, preferably industrial product, of a 3-hydroxy propanoate ester of formula (II) the said production comprising the steps of alkoxycarbonylation of a vinyl ester followed by treatment of the linear (n) product of the alkoxycarbonylation.

Despite the foregoing, the invention does not exclude the possibility of utilising the branched product of the reaction.

Therefore, according to a fourth aspect of the present invention there is provided a process for the production of a lactate ester or acid of formula III

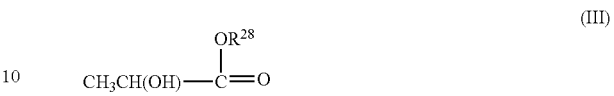

comprising the steps of alkoxycarbonylating vinyl ester with carbon monoxide in the presence of an alkanol and a catalyst system, the catalyst system obtainable by combining:
(a) a metal of Group VIII B or a compound thereof: and
(b) a bidentate ligand, preferably phosphine ligand, of general formula (I) in accordance with the first aspect as defined herein to produce a product comprising a branched (iso) product 2-acetoxy $(CH_3)$. $CH.C(O)OR^{28}$ wherein $R^{28}$ is selected from H, or a $C_1$-$C_{30}$ alkyl or aryl moiety which may be substituted or unsubstituted and either branched or linear and chemically treating the said branched (iso) product to produce the corresponding lactate or acid of formula III.

By treating or treatment herein is meant carrying out routine chemical treatment such as hydrolysis or transesterification reactions on the acetoxy product of the alkoxycarbonylation suitable to cleave the acetoxy group to produce the hydroxy acid or ester.

The linear (n) and branched (iso) products of the carbonylation may be separated either before or after the treatment step. Preferably, the products of the reaction are separated by distillation. The branched and linear products often have widely differing boiling points which makes distillation an effective separation technique for the products of the reaction.

Preferably, the ratio of linear:branched product from the alkoxycarbonylation process is greater than 1.5:1, more preferably, greater than 2:1, most preferably greater than 2.5:1.

According to a fifth aspect of the present invention there is provided the use of the catalyst system as defined in any of the $1^{st}$ or $2^{nd}$ aspects of the present invention for the production, preferably, industrial production, of a lactate ester or acid of formula (III) the said production comprising the steps of alkoxycarbonylation of a vinyl ester followed by treatment of the branched (iso) product of the alkoxycarbonylation to produce the ester or acid.

Advantageously, the lactate or 3-hydroxy propanoate esters or acids of the present invention may be hydrogenated to produce the 1,2 and 1,3 diols respectively.

Preferably, the treatment is hydrolysis or transesterification and is carried out by any suitable technique known to those skilled in the art. Such techniques are detailed in for example—"Kirkothmer Encyclopaedia of Chemical Technology", volume 9, $4^{th}$ edition page 783—"Hydrolysis of Organic Esters". Such methods include base hydrolysis, acid hydrolysis, steam hydrolysis and enzymic hydrolysis. Preferably, the hydrolysis is base hydrolysis, more preferably, the hydrolysis is carried out in excess base and then acidified to produce the acid product. Hydrogenation of the hydrolysis product may be carried out by any suitable process known to those skilled in the art. Preferably, vapour phase hydrogenation of the hydroxy alkanoate ester is carried out. A suitable technique has been exemplified in WO 01/70659 by Crabtree et al. Suitable experimental details are set out in examples 1-9 of the published application and illustrate the route to 1,3 propanediol from 3-hydroxy propanoic acid esters. Preferably, the hydrogenation is carried out in a hydrogenation zone containing a heterogenous hydrogenation catalyst. Suitable conditions and catalysts are set out in WO 01/70659, the contents of which are incorporated herein by reference insofar as they relate to the hydrogenation of 3-hydroxy propanoic acid esters. However, for the purposes of the present application such hydrogenation reactions are also deemed applicable to hydrogenation of the lactate ester to produce 1,2 propane diol. Preferably, the transesterification is carried out with the alkanol corresponding to the alkyl group of the alkyl ester product required for example methanol for converting acetoxy alkyl esters into hydroxy methyl esters and ethanol for converting acetoxy alkyl esters into hydroxy ethyl esters etc. Advantageously, this cleaves the acetoxy group but does not alter the hydroxy alkyl alkanoate. Preferably, the transesterification takes place in the presence of a suitable catalyst such as for example methane sulphonic acid or p-toluene sulphonic acid.

The group R may represent an alkylene bridging group, preferably, a lower alkylene.

In one set of embodiments the bridging group R may be defined as -A-(K,D)Ar(E,Z)—B—wherein:

Ar is a bridging group comprising an optionally substituted aryl moiety to which the $Q^1$ and $Q^2$ atoms, preferably, phosphorus atoms, are linked on available adjacent carbon atoms;

A and B each independently represent lower alkylene;

K, D, E and Z are substituents of the aryl moiety (Ar) and each independently represent hydrogen, lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$, $C(O)SR^{27}$, or -J-$Q^3(X^5)X^6$ where J represents lower alkylene; or two adjacent groups selected from K, Z, D and E together with the carbon atoms of the aryl ring to which they are attached form a further phenyl ring, which is optionally substituted by one or more substituents selected from hydrogen, lower alkyl, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$ or $C(O)SR^{27}$ or, when Ar is a cyclopentadienyl group, Z may be represented by -M($L_1$)$_n$($L_2$)$_m$ and Z is connected via a metal ligand bond to the cyclopentadienyl group;

$X^5$ represents $CR^{13}(R^{14})(R^{15})$, congressyl or adamantyl, $X^6$ represents $CR^{16}(R^{17})(R^{18})$, congressyl or adamantyl, or $X^5$ and $X^6$ together with $Q^3$ to which they are attached form an optionally substituted 2-$Q^3$-tricyclo[3.3.1.1{3,7}]decyl group or derivative thereof;

Preferably Q3 is a phospha.

Preferably in a compound of formula I when both K represents -$A_3$-$Q^3(X^5)X^6$ and E represents -$A_3$-$Q^3(X^5)X^6$, then D represents -$A_3$-$Q^3(X^5)X^6$.

The 2-meta-adamantyl group may be a 2-$Q^2$-tricyclo[3.3.1.1.{3,7}]decyl group formed by the combination of $R^1$ together with $Q^2$ to which it is attached, a 2-$Q^1$-tricyclo[3.3.1.1.{3,7}]decyl group formed by the combination of $R^2$ and $R^3$ together with $Q^1$ to which they are attached, or a 2-$Q^3$-tricyclo[3.3.1.1{3,7}]decyl group formed by the combination of $X^5$ and $X^6$ together with $Q^3$ to which they are attached respectively, wherein $Q^1$, $Q^2$ and $Q^3$ is in the 2-position of the adamantyl group of which it forms an integral part and each of $Q^1$, $Q^2$ and $Q^3$ represents phosphorus, arsenic and/or antimony. Preferably, $Q^1$, $Q^2$ and $Q^3$ represent phosphorous.

Preferred embodiments of the present invention include those wherein:

$R^2$ represents $CR^4(R^5)(R^6)$, $R^3$ represents $CR^7(R^8)(R^9)$, and $R^1$ together with $Q^2$ to which it is attached form a 2-phospha-adamantyl group;

$R^2$ represents $CR^4(R^5)(R^6)$, $R^3$ represents adamantyl, $R^1$ together with $Q^2$ to which it is attached form a 2-phospha-adamantyl group;

$R^2$ represents $CR^4(R^5)(R^6)$, $R^3$ represents congressyl, $R^1$ together with $Q^2$ to which it is attached form a 2-phospha-adamantyl group;

$R^2$ and $R^3$ independently represent adamantyl, and $R^1$ together with $Q^2$ to which it is attached form a 2-phospha-adamantyl group;

$R^2$ and $R^3$ independently represent congressyl, and $R^1$ together with $Q^2$ to which it is attached form a 2-phospha-adamantyl group;

$R^1$ together with $Q^2$ to which it is attached form a 2-phospha-adamantyl group, and $R^2$ and $R^3$ together with $Q^1$ to which they are attached form a 2-phospha-adamantyl group;

Highly preferred embodiments of the present invention include those wherein:

$R^1$ together with $Q^2$ to which it is attached form a 2-phospha-adamantyl group, and $R^2$ and $R^3$ together with $Q^1$ to which they are attached form a 2-phospha-adamantyl group;

Preferably in a compound of formula I, $R^2$ is identical to $R^3$.

Preferably, in the compound of formula I, $R^2$ and $R^3$ represent identical substituents, and $X^5$ and $X^6$ (when present) represent identical substituents, more preferably, $R^2$ and $R^3$ and $X^5$ and $X^6$ (when present) combine to be identical with $R^1$.

Particularly preferred combinations in the present invention include those wherein:—

(1) $R^1$ together with $Q^2$ to which it is attached represents 2-meta-adamantyl;
  $R^2$ and $R^3$ together with $Q^1$ to which they are attached represents 2-phospha-adamantyl;
  A and B are the same and represent —CH$_2$—;
  K, D and E are the same and represent hydrogen or unsubstituted $C_1$-$C_6$ alkyl, particularly hydrogen;
  $Q^1$ and $Q^2$ both represent phosphorus.

(2) $R^1$ together with $Q^2$ to which it is attached represents 2-meta-adamantyl;
  $R^2$ and $R^3$ together with $Q^1$ to which they are attached represents 2-meta-adamantyl;
  K represents —CH$_2$-$Q^3(X^5)X^6$ wherein $X^5$ and $X^6$ together with $Q^3$ to which they are attached represents 2-meta-adamantyl;
  A and B are the same and represent —CH$_2$—;
  $Q^1$, $Q^2$ and $Q^3$ each represent phosphorus;
  D and E are the same and represent hydrogen or unsubstituted $C_1$-$C_6$ alkyl, particularly hydrogen.

(3) $R^1$ together with $Q^2$ to which it is attached represents 2-meta-adamantyl;
  $R^2$ and $R^3$ together with $Q^1$ to which they are attached represents 2-meta-adamantyl;
  K represents —CH$_2$-$Q^3(X^5)X^6$ wherein $X^5$ and $X^6$ together with $Q^3$ to which they are attached represents 2-meta-adamantyl;
  A and B are the same and represent —CH$_2$—;
  $Q^1$, $Q^2$ and $Q^3$ each represent phosphorus.

(4) $R^1$ together with $Q^2$ to which it is attached represents 2-meta-adamantyl;
  $R^2$ and $R^3$ together with $Q^1$ to which they are attached represents 2-meta-adamantyl;
  A and B are the same and represent —$CH_2$—;
  $Q^1$ and $Q^2$ both represent phosphorus;
  K represents hydrogen or unsubstituted $C_1$-$C_6$ alkyl, particularly hydrogen;
  D and E together with the carbon atoms of the cyclopentadienyl ring to which they are attached form an unsubstituted phenyl ring;
  M represents Fe;
  n=1 and $L_1$ represents cyclopentadienyl, particularly unsubstituted cyclopentadienyl, and m=0.

(5) $R^1$ together with $Q^2$ to which it is attached represents 2-meta-adamantyl;
  $R^2$ and $R^3$ together with $Q^1$ to which they are attached represents 2-meta-adamantyl;
  A and B are the same and represent —$CH_2$—;
  K, D and E are the same and represent hydrogen or unsubstituted $C_1$-$C_6$ alkyl, particularly hydrogen;
  $Q^1$ and $Q^2$ both represent phosphorus;
  M represents Fe;
  n=1 and $L_1$ represents cyclopentadienyl, particularly unsubstituted cyclopentadienyl, and m=0.

(6) $R^1$ together with $Q^2$ to which it is attached represents 2-meta-adamantyl;
  $R^2$ and $R^3$ together with $Q^1$ to which they are attached represents 2-meta-adamantyl;
  K represents —$CH_2$-$Q^3(X^5)X^6$ wherein $X^5$ and $X^6$ together with $Q^3$ to which they are attached represents 2-meta-adamantyl;
  A and B are the same and represent —$CH_2$—;
  $Q^1$, $Q^2$ and $Q^3$ each represent phosphorus;
  D and E are the same and represent hydrogen or unsubstituted $C_1$-$C_6$ alkyl, particularly hydrogen;
  M represents Fe;
  n=1 and $L_1$ represents cyclopentadienyl, particularly unsubstituted cyclopentadienyl, and m=0.

(7) $R^1$ together with $Q^2$ to which it is attached represents 2-meta-adamantyl;
  $R^2$ and $R^3$ together with $Q^2$ to which they are attached represents 2-meta-adamantyl;
  K represents —$CH_2$-$Q^3(X^5)X^6$ wherein $X^5$ and $X^6$ together with $Q^3$ to which they are attached represents 2-meta-adamantyl;
  A and B are the same and represent —$CH_2$—;
  $Q^1$, $Q^2$ and $Q^3$ each represent phosphorus;
  D and E together with the carbon atoms of the cyclopentadienyl ring to which they are attached form an unsubstituted phenyl ring;
  M represents Fe;
  n=1 and $L_1$ represents cyclopentadienyl, particularly unsubstituted cyclopentadienyl, and m=0.

$R^4$ to $R^9$ and $R^{13}$ to $R^{18}$ each independently represent lower alkyl, aryl, or Het;

$R^{19}$ to $R^{27}$ each independently represent hydrogen, lower alkyl, aryl or Het;

M represents a Group VIB or VIIIB metal or metal cation thereof;

$L_1$ represents a cyclopentadienyl, indenyl or aryl group each of which groups are optionally substituted by one or more substituents selected from hydrogen, lower alkyl, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$, $C(O)SR^{27}$ or ferrocenyl;

$L_2$ represents one or more ligands each of which are independently selected from hydrogen, lower alkyl, alkylaryl, halo, CO, $PR^{43}R^{44}R^{45}$ or $NR^{46}R^{47}R^{48}$;

$R^{43}$ to $R^{48}$ each independently represent hydrogen, lower alkyl, aryl or Het;

n=0 or 1;

and m=0 to 5;

provided that when n=1 then m equals 0, and when n equals 0 then m does not equal 0;

$Q^3$ (when present) represents phosphorous, arsenic or antimony.

Preferably, the Group VIII B metal is palladium.

Preferably, when K, D, E or Z represent -J-$Q^3(CR^{13}(R^{14})(R^{15}))CR^{16}(R^{17})(R^{18})$, the respective K, D, E or Z is on the aryl carbon adjacent the aryl carbon to which A or B is connected or, if not so adjacent, is adjacent a remaining K, D, E or Z group which itself represents -J-$Q^3(CR^{13}(R^{14})(R^{15}))CR^{16}(R^{17})(R^{18})$.

For ease of reference, any one or more of the five aspects of the invention may be referred to herein as the process of the invention.

Suitably, the process of the invention may be used to catalyse the carbonylation of a vinyl ester in the presence of carbon monoxide and a hydroxyl group containing compound i.e. the process of the invention may catalyse the conversion of a vinyl ester to the corresponding acetoxy carboxylic ester. Conveniently, the process of the invention may utilise highly stable compounds under typical carbonylation reaction conditions such that they require little or no replenishment. Conveniently, the process of the invention may have a high rate for the carbonylation reaction of a vinyl ester. Conveniently, the process of the invention may promote high conversion rates of the vinyl ester, thereby yielding the desired product in high yield with little or no impurities. Consequently, the commercial viability of a carbonylation process, such as the carbonylation of a vinyl ester, may be increased by employing the process of the invention.

The term "Ar" or "aryl" when used herein, includes five-to-ten-membered, preferably six to ten membered, carbocyclic aromatic or pseudo aromatic groups, such as phenyl, ferrocenyl and naphthyl, which groups are optionally substituted with, in addition to K, D, E or Z, one or more substituents selected from aryl, lower alkyl (which alkyl group may itself be optionally substituted or terminated as defined below), Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$ or $C(S)NR^{25}R^{26}$ wherein $R^{19}$ to $R^{27}$ each independently represent hydrogen, aryl or lower alkyl (which alkyl group may itself be optionally substituted or terminated as defined below).

Suitably, when Ar or aryl is cyclopentadienyl and when D and E together with the carbon atoms of the cyclopentadienyl ring to which they are attached form a phenyl ring, the metal M or cation thereof is attached to an indenyl ring system. In a preferred embodiment Ar represents phenyl or naphthyl, more preferably, phenyl and in either case they may be optionally substituted as set out in the previous paragraph.

By the term "M represents a Group VIB or VIIIB metal" in a compound of formula I we include metals such as Cr, Mo, W, Fe, Co, Ni, Ru, Rh, Os, Ir, Pt and Pd. Preferably, the metals are selected from Cr, Mo, W, Fe, Co, Ni, Ru and Rh. For the avoidance of doubt, references to Group VIB or VIIIB metals herein should be taken to include Groups 6, 8, 9 and in the modern periodic table nomenclature.

By the term "metal cation thereof" we mean that the Group VIB or VIIIB metal (M) in the compound of formula I as defined herein has a positive charge. Suitably, the metal cation may be in the form of a salt or may comprise weakly coordinated anions derived from halo, nitric acid; sulphuric acid; lower alkanoic (up to $C_{12}$) acids such as acetic acid and propionic acid; sulphonic acids such as methane sulphonic acid, chlorosulphonic acid, fluorosulphonic acid, trifluoromethane sulphonic acid, benzene sulphonic acid, naphthalene sulphonic acid, toluene sulphonic acid, e.g. p-toluene sulphonic acid, t-butyl sulphonic acid, and 2-hydroxypropane sulphonic acid; sulphonated ion exchange resins; perhalic acid such as perchloric acid; perfluororated carboxylic acid such as trichloroacetic acid and trifluoroacetic acid; orthophosphoric acid; phosphonic acid such as benzene phosphonic acid; and acids derived from interactions between Lewis acids and Broensted acids. Other sources which may provide suitable anions include the tetraphenyl borate derivatives.

Preferably M represents a Group VIB or VIIIB metal. In other words the total electron count for the metal M is 18.

Halo groups, which $L_2$ may represent and with which the above-mentioned groups may be substituted or terminated, include fluoro, chloro, bromo and iodo.

Suitably, if A represents cyclopentadienyl and n=1, the compounds of formula I may contain either two cyclopentadienyl rings, two indenyl rings or one indenyl and one cyclopentadienyl ring (each of which ring systems may optionally be substituted as described herein). Such compounds may be referred to as "sandwich compounds" as the metal M or metal cation thereof is sandwiched by the two ring systems. The respective cyclopentadienyl and/or indenyl ring systems may be substantially coplanar with respect to each other or they may be tilted with respect to each other (commonly referred to as bent metallocenes).

Alternatively, when n=1, the compounds of the invention may contain either one cyclopentadienyl or one indenyl ring (each of which ring systems may optionally be substituted as described herein) and one aryl ring (i.e. $L_1$ represents aryl) which is optionally substituted as defined herein. Suitably, when n=1 and $L_1$ represents aryl then the metal M of the compounds of formula I as defined herein is typically in the form of the metal cation.

Suitably, when n=0, the compounds of the invention contain only one cyclopentadienyl or indenyl ring (each of which ring systems may optionally be substituted as described herein). Such compounds may be referred to as "half sandwich compounds". Preferably, when n=0 then m represents 1 to 5 so that the metal M of the compounds of formula I has an 18 electron count. In other words, when metal M of the compounds of formula I is iron, the total number of electrons contributed by the ligands $L_2$ is typically five.

Suitably, the metal M or metal cation thereof in the cyclopentadienyl compounds of formula I is typically bonded to the cyclopentadienyl ring(s) or the cyclopentadienyl moiety of the indenyl ring(s). Typically, the cyclopentadienyl ring or the cyclopentadienyl moiety of the indenyl ring exhibits a pentahapto bonding mode with the metal; however other bonding modes between the cyclopentadienyl ring or cyclopentadienyl moiety of the indenyl ring and the metal, such as trihapto coordination, are also embraced by the scope of the present invention.

Preferably, in the compound of formula I wherein Ar is cyclopentadienyl, M represents Cr, Mo, Fe, Co or Ru, or a metal cation thereof. Even more preferably, M represents Cr, Fe, Co or Ru or a metal cation thereof. Most preferably, M is selected from a Group VIIIB metal or metal cation thereof. An especially preferred Group VIIIB metal (M) is Fe. Although the metal M as defined herein may be in a cationic form, preferably it carries essentially no residual charge due to coordination with $L_1$ and/or $L_2$ as defined herein.

Preferably, when n=1 in the compound of formula I, $L_1$ represents cyclopentadienyl, indenyl or aryl each of which rings are optionally substituted by one or more substituents selected from hydrogen, lower alkyl, halo, cyano, $OR^{19}$, $OC(O)R^{20}$, $C(O)R^{21}$, $C(O)OR^{22}$, $NR^{23}R^{24}$, $SR^{27}$ or ferrocenyl (by which is meant the cyclopentadienyl, indenyl or aryl ring which $L_1$ may represent is bonded directly to the cyclopentadienyl ring of the metallocenyl group). More preferably, if the cyclopentadienyl, indenyl or aryl ring which $L_1$ may represent is substituted it is preferably substituted with one or more substituents selected from $C_1$-$C_6$ alkyl, halo, cyano, $OR^{19}$, $OC(O)R^{20}$, $C(O)R^{21}$, $C(O)OR^{22}$, $NR^{23}R^{24}$ where $R^{19}$, $R^{20}$, $R^{21}$, $R^{22}$, $R^{23}$ and $R^{24}$ each independently represent hydrogen or $C_1$-$C_6$ alkyl.

Preferably, when n=1, $L_1$ represents cyclopentadienyl, indenyl, phenyl or naphthyl optionally substituted as defined herein. Preferably, the cyclopentadienyl, indenyl, phenyl or naphthyl groups are unsubstituted. More preferably, $L_1$ represents cyclopentadienyl, indenyl or phenyl, each of which rings are unsubstituted. Most preferably, $L_1$ represents unsubstituted cyclopentadienyl.

In a particularly preferred embodiment of the present invention, in a compound of formula I, n=1, $L_1$ is as defined herein and m=0.

Alternatively, when n is equal to zero and m is not equal to zero in a compound of formula I, $L_2$ represents one or more ligands each of which are independently selected from lower alkyl, halo, CO, $PR^{43}R^{44}R^{45}$ or $NR^{46}R^{47}R^{48}$. More preferably, $L_2$ represents one or more ligands each of which are independently selected from $C_1$ to $C_4$ alkyl, halo, particularly chloro, CO, $PR^{43}R^{44}R^{45}$ or $NR^{46}R^{47}$, wherein $R^{43}$ to $R^{48}$ are independently selected from hydrogen, $C_1$ to $C_6$ alkyl or aryl, such as phenyl.

In a particularly preferred alternative embodiment of the present invention, in a compound of formula I, n=0, $L_2$ is as defined herein and m=3 or 4, particularly 3.

M represents a metal selected from Cr, Mo, Fe, Co or Ru or a metal cation thereof;

$L_1$ represents cyclopentadienyl, indenyl, naphthyl or phenyl, each of which rings may be optionally substituted by one or more substituents selected from $C_1$-$C_6$ alkyl, halo, cyano, $OR^{19}$, $OC(O)R^{20}$, $C(O)R^{21}$, $C(O)R^{22}$, $NR^{23}R^{24}$;

$L_2$ represents one or more ligands each of which ligands are independently selected from $C_1$-$C_6$ alkyl, halo, CO, $PR^{43}R^{44}R^{45}$ or $NR^{46}R^{47}R^{48}$;

n=0 or 1;

and m=0 to 4;

provided that when n=1 then m=0 and when m does not equal zero then n=0.

Further preferred compounds of formula I include those wherein:

M represents iron or a cation thereof;

$L_1$ represents cyclopentadienyl, indenyl or phenyl group, each of which groups are optionally substituted by one or more substituents selected from $C_1$-$C_6$ alkyl, halo, cyano, $OR^{19}$, $OC(O)R^{20}$, $C(O)R^{21}$, $C(O)R^{22}$;

$L_2$ represents one or more ligands each of which are independently selected from $C_1$-$C_6$ alkyl, halo, CO, $PR^{43}R^{44}R^{45}$ or $NR^{46}R^{47}R^{48}$, where $R^{43}$ to $R^{48}$ are independently selected from hydrogen, $C_1$-$C_6$ alkyl or phenyl;

n=0 or 1; and m=0 to 4.

Still further preferred compounds of formula I include those wherein:

$L_1$ represents unsubstituted cyclopentadienyl, indenyl or phenyl, particularly unsubstituted cyclopentadienyl; and, n=1 and m=0.

Alternative preferred compounds of formula I include those wherein:

n=0;

$L_2$ represents one or more ligands each of which are independently selected from $C_1$ to $C_6$ alkyl, halo, CO, $PR^{43}R^{44}R^{45}$ or $NR^{46}R^{47}R^{48}$, where $R^{43}$ to $R^{48}$ are independently selected from hydrogen, $C_1$-$C_6$ alkyl or phenyl; and m=1 to 4, particularly 3 or 4. For example, when m=3 the three ligands which $L_2$ may represent include $(CO)_2$halo, $(PR^{43}R^{44}R^{45})_2$halo or $(NR^{46}R^{47}R^{48})_2$halo.

References to vinyl ester herein include references to substituted or unsubstituted vinyl acetate of formula (IV):

$$R^{29}\text{---}C(O)OCR^{30}\!\!=\!\!CR^{31}R^{32}$$

wherein $R^{29}$ may be selected from hydrogen, lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)\ R^{25}R^{26}$, $SR^{27}$, $C(O)\ SR^{29}$ wherein $R^{19}$-$R^{27}$ are as defined herein.

Preferably, $R^{29}$ is selected from hydrogen, lower alkyl, phenyl or lower alkylphenyl. More preferably, hydrogen, phenyl, $C_1$-$C_6$ alkylphenyl or $C_1$-$C_6$ alkyl, such as methyl, ethyl, propyl, butyl, pentyl and hexyl, even more preferably, $C_1$-$C_6$ alkyl, especially methyl.

Preferably, $R^{30}$-$R^{32}$ each independently represent hydrogen, lower alkyl, aryl or Het as defined herein. Most preferably, $R^{30}$-$R^{32}$ represent hydrogen. As mentioned above, $R^{28}$ may be optionally substituted, preferably, with one or more substituents selected from lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$ or $C(O)SR^{27}$ as defined herein.

$R^{28}$ is most preferably the alkyl/aryl group derived from a $C_1$-$C_8$ alkanol such as methanol, ethanol, propanol, iso-propanol, iso-butanol, t-butyl alcohol, n-butanol, phenol and chlorocapryl alcohol. The most preferred groups are methyl and ethyl, the most especially preferred group is methyl.

The term "Het", when used herein, includes four-to-twelve-membered, preferably four-to-ten-membered ring systems, which rings contain one or more heteroatoms selected from nitrogen, oxygen, sulphur and mixtures thereof, and which rings may contain one or more double bonds or be non-aromatic, partly aromatic or wholly aromatic in character. The ring systems may be monocyclic, bicyclic or fused. Each "Het" group identified herein is optionally substituted by one or more substituents selected from halo, cyano, nitro, oxo, lower alkyl (which alkyl group may itself be optionally substituted or terminated as defined below) $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$ or $C(S)NR^{25}R^{26}$ wherein $R^1$ to $R^{27}$ each independently represent hydrogen, aryl or lower alkyl (which alkyl group itself may be optionally substituted or terminated as defined below). The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl. Substitution at Het may be at a carbon atom of the Het ring or, where appropriate, at one or more of the heteroatoms.

"Het" groups may also be in the form of an N oxide.

The term "lower alkyl" when used herein, means $C_1$ to $C_{10}$ and includes methyl, ethyl, propyl, butyl, pentyl, hexyl and heptyl groups. Unless otherwise specified, alkyl groups may, when there is a sufficient number of carbon atoms, be linear or branched, be saturated or unsaturated, be cyclic, acyclic or part cyclic/acyclic, and/or be substituted or terminated by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, aryl or Het, wherein $R^{19}$ to $R^{27}$ each independently represent hydrogen, aryl or lower alkyl, and/or be interrupted by one or more oxygen or sulphur atoms, or by silano or dialkylsilcon groups.

Lower alkyl groups or alkyl groups which $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}R^{29}$, $R^{30}$, $R^{31}$, $R^{32}$, K, D, E and Z may represent and with which aryl and Het may be substituted, may, when there is a sufficient number of carbon atoms, be linear or branched, be saturated or unsaturated, be cyclic, acyclic or part cyclic/acyclic, and/or be interrupted by one or more of oxygen or sulphur atoms, or by silano or dialkylsilicon groups, and/or be substituted by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, aryl or Het wherein $R^{19}$ to $R^{27}$ each independently represent hydrogen, aryl or lower alkyl.

Similarly, the term "lower alkylene" which R, A, B and J (when present) represent in a compound of formula I, when used herein, includes $C_1$ to $C_{10}$ groups which can be bonded at two places on the group and is otherwise defined in the same way as "lower alkyl".

Halo groups with which the above-mentioned groups may be substituted or terminated include fluoro, chloro, bromo and iodo.

Where a compound of a formula herein (eg. formulas I-IV) contains an alkenyl group, cis (E) and trans (Z) isomerism may also occur. The present invention includes the individual stereoisomers of the compounds of any of the formulas defined herein and, where appropriate, the individual tautomeric forms thereof, together with mixtures thereof. Separation of diastereoisomers or cis and trans isomers may be achieved by conventional techniques, e.g. by fractional crystallisation, chromatography or H.P.L.C. of a stereoisomeric mixture of a compound one of the formulas or a suitable salt or derivative thereof. An individual enantiomer of a compound of one of the formulas may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

All stereoisomers are included within the scope of the process of the invention.

It will be appreciated by those skilled in the art that the compounds of formula I (b) may function as ligands that coordinate with the Group VIIIB metal or compound thereof (a) to form the compounds for use in the invention. Typically, the Group VIIIB metal or compound thereof (a) coordinates to the one or more phosphorous, arsenic and/or antimony atoms of the compound of formula I.

Preferably, $R^4$ to $R^9$, $R^{13}$ to $R^{18}$ and $R^{28}$ each independently represent lower alkyl or aryl. More preferably, $R^4$ to $R^9$, $R^{13}$ to $R^{18}$ and $R^{28}$ each independently represent $C_1$ to $C_6$ alkyl, $C_1$-$C_6$ alkyl phenyl (wherein the phenyl group is optionally substituted as defined herein) or phenyl (wherein the phenyl group is optionally substituted as defined herein). Even more preferably, $R^4$ to $R^9$, $R^{13}$ to $R^{18}$ or $R^{28}$ each independently represent $C_1$ to $C_6$ alkyl, which is optionally substituted as defined herein. Most preferably, $R^4$ to $R^9$, $R^{13}$ to $R^{18}$ or $R^{28}$ each represent non-substituted $C_1$ to $C_6$ alkyl such as methyl, ethyl, n-propyl, iso-propyl, n-butyl, iso-butyl, tert-butyl, pentyl, hexyl and cyclohexyl.

Alternatively, or additionally, each of the groups $R^4$ to $R^6$, $R^7$ to $R^9$, $R^{13}$ to $R^{15}$ or $R^{16}$ to $R^{18}$ together independently may form cyclic structures such as 1-norbornyl or 1-norbornadienyl. Further examples of composite groups include cyclic structures formed between $R^4$-$R^9$ and $R^{13}$-$R^{18}$. Alternatively, one or more of the groups may represent a solid phase to which the ligand is attached.

In a particularly preferred embodiment of the present invention $R^4$, $R^7$, $R^{13}$ and $R^{16}$ each represent the same lower alkyl, aryl or Het moiety as defined herein, $R^5$, $R^8$, $R^{14}$ and $R^{17}$ each represent the same lower alkyl, aryl or Het moiety as defined herein, and $R^6$, $R^9$, $R^{15}$ and $R^{18}$ each represent the same lower alkyl, aryl or Het moiety as defined herein. More preferably $R^4$, $R^7$, $R^{13}$ and $R^{16}$ each represent the same $C_1$-$C_6$ alkyl, particularly non-substituted $C_1$-$C_6$ alkyl, such as methyl, ethyl, n-propyl, iso-propyl, n-butyl, iso-butyl, tert-butyl, pentyl, hexyl or cyclohexyl; $R^5$, $R^8$, $R^{14}$ and $R^{17}$ each independently represent the same $C_1$-$C_6$ alkyl as defined above; and $R^6$, $R^9$, $R^{15}$ and $R^{18}$ each independently represent the same $C_1$-$C_6$ alkyl as defined above. For example: $R^4$, $R^7$, $R^{13}$ and $R^{16}$ each represent methyl; $R^5$, $R^8$, $R^{14}$ and $R^{17}$ each represent ethyl; and, $R^6$, $R^9$, $R^{15}$ and $R^{18}$ each represent n-butyl or n-pentyl.

In an especially preferred embodiment of the present invention each $R^4$ to $R^9$, $R^{13}$ to $R^{18}$ and $R^{28}$ group represents the same lower alkyl, aryl, or Het moiety as defined herein. Preferably, when alkyl groups, each $R^4$ to $R^9$, $R^{13}$ to $R^{18}$ represents the same $C_1$ to $C_6$ alkyl group, particularly non-substituted $C_1$-$C_6$ alkyl, such as methyl, ethyl, n-propyl, iso-propyl, n-butyl, iso-butyl, tert-butyl, pentyl, hexyl and cyclohexyl. Most preferably, each $R^4$ to $R^9$, $R^{13}$ to $R^{18}$ and $R^{28}$ represents methyl.

In the compound of formula I, preferably each $Q^1$, $Q^2$ and $Q^3$ (when present) are the same. Most preferably, each $Q^1$, $Q^2$ and $Q^3$ (when present) represents phosphorous.

Preferably, in the compound of formula I, R (when alkylene), A, B and J (when present) each independently represent $C_1$ to $C_6$ alkylene which is optionally substituted as defined herein, for example with lower alkyl groups. Preferably, the lower alkylene groups which R (when alkylene), A, B and J (when present) represent are non-substituted. A particular preferred lower alkylene which A, B and J may independently represent is —$CH_2$— or —$C_2H_4$—. Most preferably, each of A, B and J (when present) represent the same lower alkylene as defined herein, particularly —$CH_2$—. Particularly preferred lower alkylenes which R represents may be selected from ethylene (—$C_2H_4$—), propylene (—$C_4H_6$—) and butylene (—$C_4H_8$—), more preferably, ethylene or propylene, most preferably, propylene.

Preferably, in the compound of formula I when K, D, E or Z does not represent -J-$Q^3$($CR^{13}$($R^{14}$)($R^{15}$))$CR^{16}$($R^{17}$)($R^{18}$), K, D, E or Z represents hydrogen, lower alkyl, phenyl or lower alkylphenyl. More preferably, K, D, E or Z represent hydrogen, phenyl, $C_1$-$C_6$ alkylphenyl or $C_1$-$C_6$ alkyl, such as methyl, ethyl, propyl, butyl, pentyl and hexyl. Most preferably, K, D, E or Z represents hydrogen.

Preferably, in the compound of formula I when K, D, E and Z together with the carbon atoms of the aryl ring to which they are attached do not form a phenyl ring, K, D, E and Z each independently represent hydrogen, lower alkyl, phenyl or lower alkylphenyl. More preferably, K, D, E and Z each independently represent hydrogen, phenyl, $C_1$-$C_6$ alkylphenyl or $C_1$-$C_6$ alkyl, such as methyl, ethyl, propyl, butyl, pentyl and hexyl. Even more preferably, K, D, E and Z represent the same substituent. Most preferably, they represent hydrogen.

Preferably, in the compound of formula I when K, D, E or Z does not represent -J-$Q^3$($CR^{13}$($R^{14}$)($R^{15}$))$CR^{16}$($R^{17}$)($R^{18}$) and K, D, E and Z together with the carbon atoms of the aryl ring to which they are attached do not form a phenyl ring, each of K, D, E and Z represent the same group selected from hydrogen, lower alkyl, aryl, or Het as defined herein; particularly hydrogen or $C_1$-$C_6$ alkyl (more particularly unsubstituted $C_1$-$C_6$ alkyl), especially hydrogen.

Preferably, in the compound of formula I when two of K, D, E and Z together with the carbon atoms of the aryl ring to which they are attached form a phenyl ring, then the phenyl ring is optionally substituted with one or more substituents selected from aryl, lower alkyl (which alkyl group may itself be optionally substituted or terminated as defined below), Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$ or $C(S)NR^{25}R^{26}$ wherein $R^{19}$ to $R^{27}$ each independently represent hydrogen or lower alkyl (which alkyl group may itself be optionally substituted or terminated as defined herein). More preferably, the phenyl ring is not substituted by any substituents i.e. it bears hydrogen atoms only.

Preferred compounds of formula I include those wherein:

A and B each independently represent unsubstituted $C_1$ to $C_6$ alkylene;

K, D, Z and E each independently represent hydrogen, $C_1$-$C_6$ alkyl, phenyl, $C_1$-$C_6$ alkylphenyl or -J-$Q^3$($CR^{13}$($R^{14}$)($R^{15}$))$CR^{16}$($R^{17}$)($R^{18}$) where J represents unsubstituted $C_1$ to $C_6$ alkylene; or two of K, D, Z and E together with the carbon atoms of the aryl ring to which they are attached form a phenyl ring which is optionally substituted by one or more substituents selected from lower alkyl, phenyl or lower alkylphenyl.

$R^4$ to $R^9$ and $R^{13}$ to $R^{18}$ each independently represent $C_1$ to $C_6$ alkyl, phenyl or $C_1$ to $C_6$ alkylphenyl.

Further preferred compounds of formula I include those wherein:

A and B both represent —$CH_2$— or $C_2H_4$, particularly $CH_2$;

K, D, Z and E each independently represent hydrogen, $C_1$-$C_6$ alkyl phenyl or $C_1$-$C_6$ alkyl or -J-$Q^3$($CR^{13}$($R^{14}$)($R^{15}$))$CR^{16}$($R^{17}$)($R^{18}$) where J is the same as A; or two of K, D, E and Z together with the carbon atoms of the aryl ring to which they are attached form an unsubstituted phenyl ring;

$R^4$ to $R^9$ and $R^{13}$ to $R^{18}$ each independently represent $C_1$ to $C_6$ alkyl;

Still further preferred compounds of formula I include those wherein:

$R^4$ to $R^9$ and $R^{13}$ to $R^{18}$ are alkylene and are the same and each represents $C_1$ to $C_6$ alkyl, particularly methyl.

Still further preferred compounds of formula I include those wherein:

K, D, Z and E are each independently selected from the group consisting of hydrogen or $C_1$ to $C_6$ alkyl, particularly where each of K, D, Z and E represent the same group, especially where each of K, D, Z and E represent hydrogen; or K represents —$CH_2$-$Q^3$($CR^{13}$($R^{14}$)($R^{15}$))$CR^{16}$($R^{17}$)($R^{18}$) and D, Z and E are each independently selected from the group consisting of hydrogen or $C_1$ to $C_6$ alkyl, particularly where both D and E represent the same group, especially where D, Z and E represent hydrogen.

Especially preferred specific compounds of formula I include those wherein:

each $R^4$ to $R^9$ is the same and represents methyl;

A and B are the same and represent —$CH_2$—;

K, D, Z and E are the same and represent hydrogen.

The present invention provides a process for the carbonylation of a vinyl ester comprising contacting a vinyl ester with carbon monoxide and a alkanol in the presence of a catalyst compound as defined in the present invention.

Suitably, the alkanol includes an organic molecule having a hydroxyl functional group. Preferably, the organic molecule having a hydroxyl functional group may be branched or linear, and comprises an alkanol, particularly a $C_1$-$C_{30}$ alkanol, including aryl alkanols, which may be optionally substituted with one or more substituents selected from lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$ or $C(O)SR^{27}$ as defined herein. Highly preferred alkanols are $C_1$-$C_8$ alkanols such as methanol, ethanol, propanol, iso-propanol, iso-butanol, t-butyl alcohol, n-butanol, phenol and chlorocapryl alcohol. Although the monoalkanols are most preferred, poly-alkanols, preferably, selected from di-octa ols such as diols, triols, tetra-ols and sugars may also be utilised. Typically, such polyalkanols are selected from 1,2-ethanediol, 1,3-propanediol, glycerol, 1,2,4 butanetriol, 2-(hydroxymethyl)-1,3-propanediol, 1,2,6 trihydroxyhexane, pentaerythritol, 1,1,1 tri(hydroxymethyl)ethane, nannose, sorbase, galactose and other sugars. Preferred sugars include sucrose, fructose and glucose. Especially preferred alkanols are methanol and ethanol. The most preferred alkanol is methanol.

The amount of alcohol is not critical. Generally, amounts are used in excess of the amount of vinyl ester compound to be carbonylated. Thus the alcohol may serve as the reaction solvent as well, although, if desired, separate solvents may also be used.

It will be appreciated that the end product of the reaction is determined at least in part by the source of alkanol used. Use of methanol conveniently produces the 2-acetoxy methyl propanoate or 3-acetoxymethyl propanoate.

In the process according to the present invention, the carbon monoxide may be used in pure form or diluted with an inert gas such as nitrogen, carbon dioxide or a noble gas such as argon. Small amounts of hydrogen, typically less than 5% by volume, may also be present.

The ratio (volume/volume) of vinyl ester to alkanol may vary between wide limits and suitably lies in the range of 1:0.1 to 1:10, preferably from between 2:1 to 1:2 and up to a large excess of alkanol when the latter is also the reaction solvent such as up to a 50:1 excess of alkanol.

The amount of the catalyst of the invention used in the carbonylation process of the vinyl ester is not critical. Good results may be obtained when, preferably, the amount of Group VIII B metal is in the range $10^{-7}$ to $10^{-1}$ moles per mole of vinyl ester, more preferably, $10^{-6}$ to $10^{-2}$ moles, most preferably $10^{-5}$ to $10^{-2}$ moles per mole of ester. Preferably, the amount of bidentate compound of formula I to unsaturated compound is in the range $10^{-7}$ to $10^{-1}$, more preferably, $10^{-6}$ to $10^{-2}$, most preferably, $10^{-5}$ to $10^{-2}$ moles per mole of vinyl ester.

Suitably, although non-essential to the invention, the carbonylation of a vinyl ester as defined herein may be performed in one or more aprotic solvents. Suitable solvents include ketones, such as for example methylbutylketone; ethers, such as for example anisole (methyl phenyl ether), 2,5,8-trioxanonane (diglyme), diethyl ether, dimethyl ether, tetrahydrofuran, diphenylether, diisopropylether and the dimethylether of di-ethylene-glycol; esters, such as for example methylacetate, dimethyladipate methyl benzoate, dimethyl phthalate and butyrolactone; amides, such as for example dimethylacetamide, N-methylpyrrolidone and dimethyl formamide; sulfoxides and sulphones, such as for example dimethylsulphoxide, di-isopropylsulphone, sulfolane (tetrahydrothiophene-2,2-dioxide), 2-methylsulfolane, diethyl sulphone, tetrahydrothiophene 1,1-dioxide and 2-methyl-4-ethylsulfolane; aromatic compounds, including halo variants of such compounds eg. benzene, toluene, ethyl benzene o-xylene, m-xylene, p-xylene, chlorobenzene, o-dichlorobenzene, m-dichlorobenzene: alkanes, including halo variants of such compounds eg, hexane, heptane, 2,2,3-trimethylpentane, methylene chloride and carbon tetrachloride; nitriles eg. benzonitrile and acetonitrile.

Very suitable are aprotic solvents having a dielectric constant that is below a value of 50, more preferably in the range of 3 to 8, at 298.15 K and $1 \times 10^5 Nm^{-2}$. In the present context, the dielectric constant for a given solvent is used in its normal meaning of representing the ratio of the capacity of a condenser with that substance as dielectric to the capacity of the same condenser with a vacuum for dielectric. Values for the dielectric constants of common organic liquids can be found in general reference books, such as the Handbook of Chemistry and Physics, $76^{th}$ edition, edited by David R. Lide et al, and published by CRC press in 1995, and are usually quoted for a temperature of about 20° C. or 25° C., i.e. about 293.15k or 298.15 K, and atmospheric pressure, i.e. about $1 \times 10^5 Nm^{-2}$, or can readily be converted to that temperature and pressure using the conversion factors quoted. If no literature data for a particular compound is available, the dielectric constant may be readily measured using established physico-chemical methods.

For example, the dielectric constant of anisole is 4.3 (at 294.2 K), of diethyl ether is 4.3 (at 293.2 K), of sulfolane is 43.4 (at 303.2 K), of methylpentanoate is 5.0 (at 293.2 K), of diphenylether is 3.7 (at 283.2 K), of dimethyladipate is 6.8 (at 293.2 K), of tetrahydrofuran is 7.5 (at 295.2 K), of methylnonanoate is 3.9 (at 293.2 K). A preferred solvent is anisole.

Due to the alkanol, an aprotic solvent will be generated by the reaction as the ester carbonylation product of the vinyl ester, carbon monoxide and the alkanol is an aprotic solvent.

The process may be carried out in an excess of aprotic solvent, i.e. at a ratio (v/v) of aprotic solvent to alkanol of at least 1:1. Preferably, this ratio ranges from 1:1 to 10:1 and more preferably from 1:1 to 5:1. Most preferably the ratio (v/v) ranges from 1.5:1 to 3:1.

Despite the aforegoing it is preferred that the reaction is carried out in the absence of any external added aprotic solvent ie. an aprotic solvent not generated by the reaction itself.

The catalyst compounds of the present invention may act as a "heterogeneous" catalyst or a "homogeneous" catalyst.

By the term "homogeneous" catalyst we mean a catalyst, i.e. a compound of the invention, which is not supported but is simply admixed or formed in-situ with the reactants of the carbonylation reaction (e.g. the vinyl ester, the hydroxyl containing compound and carbon monoxide), preferably in a suitable solvent as described herein.

By the term "heterogeneous" catalyst we mean a catalyst, i.e. the compound of the invention, which is carried on a support.

Thus according to a further aspect, the present invention provides a process for the carbonylation of vinyl esters as defined herein wherein the process is carried out with the catalyst comprising a support, preferably an insoluble support.

Preferably, the support comprises a polymer such as a polyolefin, polystyrene or polystyrene copolymer such as a divinylbenzene copolymer or other suitable polymers or copolymers known to those skilled in the art; a silicon derivative such as a functionalised silica, a silicone or a silicone rubber; or other porous particulate material such as for example inorganic oxides and inorganic chlorides.

Preferably the support material is porous silica which has a surface area in the range of from 10 to 700 $m^2/g$, a total pore volume in the range of from 0.1 to 4.0 cc/g and an average particle size in the range of from 10 to 500 µm. More preferably, the surface area is in the range of from 50 to 500 $m^2/g$, the pore volume is in the range of from 0.5 to 2.5 cc/g and the average particle size is in the range of from 20 to 200 µm. Most desirably the surface area is in the range of from 100 to 400 $m^2/g$, the pore volume is in the range of from 0.8 to 3.0 cc/g and the average particle size is in the range of from 30 to 100 µm. The average pore size of typical porous support materials is in the range of from 10 to 1000 Å. Preferably, a support material is used that has an average pore diameter of from 50 to 500 Å, and most desirably from 75 to 350 Å. It may be particularly desirable to dehydrate the silica at a temperature of from 100° C. to 800° C. anywhere from 3 to 24 hours.

Suitably, the support may be flexible or a rigid support, the insoluble support is coated and/or impregnated with the compounds of the process of the invention by techniques well known to those skilled in the art.

Alternatively, the compounds of the process of the invention are fixed to the surface of an insoluble support, optionally via a covalent bond, and the arrangement optionally includes a bifunctional spacer molecule to space the compound from the insoluble support.

The compounds of the invention may be fixed to the surface of the insoluble support by promoting reaction of a functional group present in the compound of formula I, for example a substituent K, D, Z and E of the aryl moiety, with a complimentary reactive group present on or previously inserted into the support. The combination of the reactive group of the support with a complimentary substituent of the compound of the invention provides a heterogeneous catalyst where the compound of the invention and the support are linked via a linkage such as an ether, ester, amide, amine, urea, keto group.

The choice of reaction conditions to link a compound of the process of the present invention to the support depend upon the vinyl ester and the groups of the support. For example, reagents such as carbodiimides, 1,1-carbonyldiimidazole, and processes such as the use of mixed anhydrides, reductive amination may be employed.

According to a further aspect, the present invention provides the use of the process of any aspect of the invention wherein the catalyst is attached to a support.

Particularly preferred is when the organic groups $R^4$, $R^5$, $R^6$, $R^7$, $R^8$, $R^9$, or $R^{13}$-$R^{18}$ when associated with their respective carbon atom form composite groups which are at least as sterically hindering as t-butyl. Steric hindrance in this context is as discussed at page 14 et seq of "Homogenous Transition Metal Catalysis—A Gentle Art", by C Masters, published by Chapman and Hall 1981. These steric groups may be cyclic, part-cyclic or acyclic. When cyclic or part cyclic, the group may be substituted or unsubstituted or be saturated or unsaturated. The cyclic or part cyclic groups may contain, including the tertiary carbon atom, from $C_4$-$C_{30}$, more preferably $C_6$-$C_{20}$, most preferably $C_{10}$-$C_{15}$ carbon atoms in the cyclic structure. The cyclic structure may be substituted by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, aryl or Het, wherein $R^{19}$ to $R^{27}$ each independently represent hydrogen, aryl or lower alkyl, and/or be interrupted by one or more oxygen or sulphur atoms, or by silano or dialkylsilcon groups.

The bridging group Ar is an aryl moiety, eg. a phenyl group, which may be optionally substituted, provided that the two phosphorus atoms are linked to adjacent carbon atoms, eg. at the 1 and 2 positions on the phenyl group. Furthermore, the aryl moiety may be a fused polycyclic group eg. naphthalene, biphenylene or indene.

Examples of suitable bidentate ligands are 1,2-bis(2-phosphinomethyl-1,3,5,7-tetramethyl-6,9,10-trioxa-adamantyl) ferrocene, 1,2-bis(2-phosphinomethyl-1,3,5,7-tetramethyl-6,9,10-trioxa-adamantyl)benzene, 1,2,3-tris-(2-phosphinomethyl-1,3,5,7-tetramethyl-6,9,10-trioxa-adamantyl)ferrocene; 1-(2-phosphinomethyl-1,3,5,7-tetramethyl-6,9,10-trioxa-adamantyl)-2-(di-t-butylphosphinomethyl)benzene;

1-(2-phosphinomethyl-1,3,5,7-tetramethyl-6,9,10-trioxa-adamantyl)-2-(diadamantylphosphinomethyl)benzene; 1,2 bis(2-phosphinomethyl-1,3,5,7-tetramethyl-6,9,10-trioxa-adamantyl)naphthalene;

1,2-P,P'-di(2-phospha-1,3,5,7-tetramethyl-6,9,10-trioxatricyclo-{3.3.1.1[3.7]}decyl)ethane (DPA2); 1,3-P,P'-di(2-phospha-1,3,5,7-tetramethyl-6,9,10-trioxatricyclo{3.3.1.1 [3.7]}-decyl)propane (DPA3); 1,2-P,P'-di-perfluoro(2-phospha-1,3,5,7-tetramethyl-6,9,10-trioxatricyclo{3.3.1.1 [3.7]}-decyl)ethane; 1,3-P,P'-di-perfluoro(2-phospha-1,3,5, 7-tetramethyl-6,9,10-trioxatricyclo {3.3.1.1[3.7]}decyl)-propane; 1,2-P,P'-di-(2-phospha-1,3,5,7-tetra(trifluoromethyl)-6,9,10-trioxatricyclo {3.3.1.1[3.7]}decyl)ethane and 1,3-P,P'-di-(2-phospha-1,3,5,7-tetra(trifluoro-methyl)-6, 9,10-trioxatricyclo {3.3.1.1[3.7]}decyl)propane, DPA3 being most preferred.

Additionally, the bidentate phosphine may be bonded to a suitable polymeric substrate via at least one of the bridging group Ar, the linking group A or the linking group B eg. bis(2-phosphino-1,3,5,7-tetramethyl-6,9,10-trioxa-adamantyl)-o-xylene may be bonded via the xylene group to polystyrene to give an immobile heterogeneous catalyst.

The amount of bidentate ligand used can vary within wide limits. Preferably, the bidentate ligand is present in an amount such that the ratio of the number of moles of the bidentate ligand present to the number of moles of the Group VIII metal present is from 1 to 50 eg. 1 to 10 and particularly from 1 to 5 mol per mol of metal. More preferably, the mol:mol range of compounds of formula I to Group VIIIB metal is in the range of 1:1 to 3:1, most preferably in the range of 1:1 to 1.5:1. Conveniently, the possibility of applying these low molar ratios is advantageous, as it avoids the use of an excess of the compound of formula I and hence minimises the consumption of these usually expensive compounds. Suitably, the catalysts of the invention are prepared in a separate step preceding their use in-situ in the carbonylation reaction of a vinyl ester.

Conveniently, the process of the invention may be carried out by dissolving the Group VIIIB metal or compound thereof as defined herein in a suitable solvent such as one of the alkanols or aprotic solvents previously described (a particularly preferred solvent would be the ester or acid product of the specific carbonylation reaction eg. Methyl lactate for vinyl acetate carbonylation) and subsequently admixing with a compound of formula I as defined herein.

The carbon monoxide may be used in the presence of other gases which are inert in the reaction. Examples of such gases include hydrogen, nitrogen, carbon dioxide and the noble gases such as argon.

The molar ratio of the amount of vinyl ester used in the reaction to the amount of alkanol is not critical and may vary between wide limits, eg. from 0.001:1 to 100:1 mol/mol.

The product of the reaction may be separated from the other components by any suitable means. However, it is an advantage of the present process that significantly fewer by-products are formed thereby reducing the need for further purification after the initial separation of the product as may be evidenced by the generally significantly higher selectivity. A further advantage is that the other components which contain the catalyst system which may be recycled and/or reused in further reactions with minimal supplementation of fresh catalyst.

Preferably, the carbonylation is carried out at a temperature of between −10 to 150° C., more preferably 0° C. to 140° C., most preferably 20° C. to 120° C. An especially preferred temperature is one chosen between 80° C. to 120° C. Advantageously, the carbonylation can be carried out at moderate temperatures, it is particularly advantageous to be able to carry out the reaction at room temperature (20° C.).

Preferably, when operating a low temperature carbonylation, the carbonylation is carried out between −30° C. to 49° C., more preferably, −10° C. to 45° C., still more preferably 0° C. to 45° C., most preferably 10° C. to 45° C. Especially preferred is a range of 10 to 35° C.

Preferably, the carbonylation is carried out at a CO partial pressure of between $0.80 \times 10^5$ $N.m^{-2}$-$90 \times 10^5 N.m^{-2}$, more preferably $1 \times 10^5$ $N.m^{-2}$–$65 \times 10^5 N.m^{-2}$, most preferably $1$-$30 \times 10^5 N.m^{-2}$. Especially preferred is a CO partial pressure of 5 to $20 \times 10^5 N.m^{-2}$.

Preferably, a low pressure carbonylation is also envisaged. Preferably, when operating a low pressure carbonylation the carbonylation is carried out at a CO partial pressure of between 0.1 to $5 \times 10^5 N.m^{-2}$, more preferably 0.2 to $2 \times 10^5 N.m^{-2}$, most preferably 0.5 to $1.5 \times 10^5 N.m^{-2}$.

The catalyst system of the present invention is preferably constituted in the liquid phase which may be formed by one or more of the reactants or by the use of a suitable solvent.

As mentioned above, vinyl acetate can be substituted or non-substituted. However, it is preferred that the vinyl acetate is unsubstituted.

The use of stabilising compounds with the catalyst system may also be beneficial in improving recovery of metal which has been lost from the catalyst system. When the catalyst system is utilized in a liquid reaction medium such stabilizing compounds may assist recovery of the group VIIIB metal.

Preferably, therefore, the catalyst system includes in a liquid reaction medium a polymeric dispersant dissolved in a liquid carrier, said polymeric dispersant being capable of stabilising a colloidal suspension of particles of the group VIIIB metal or metal compound of the catalyst system within the liquid carrier.

The liquid reaction medium may be a solvent for the reaction or may comprise one or more of the reactants or reaction products themselves. The reactants and reaction products in liquid form may be miscible with or dissolved in a solvent or liquid diluent.

The polymeric dispersant is soluble in the liquid reaction medium, but should not significantly increase the viscosity of the reaction medium in a way which would be detrimental to reaction kinetics or heat transfer. The solubility of the dispersant in the liquid medium under the reaction conditions of temperature and pressure should not be so great as to deter significantly the adsorption of the dispersant molecules onto the metal particles.

The polymeric dispersant is capable of stabilising a colloidal suspension of particles of said group VIIIB metal or metal compound within the liquid reaction medium such that the metal particles formed as a result of catalyst degradation are held in suspension in the liquid reaction medium and are discharged from the reactor along with the liquid for reclamation and optionally for re-use in making further quantities of catalyst. The metal particles are normally of colloidal dimensions, e.g. in the range 5-100 nm average particle size although larger particles may form in some cases. Portions of the polymeric dispersant are adsorbed onto the surface of the metal particles whilst the remainder of the dispersant molecules remain at least partially solvated by the liquid reaction medium and in this way the dispersed group VIIIB metal particles are stabilised against settling on the walls of the reactor or in reactor dead spaces and against forming agglomerates of metal particles which may grow by collision of particles and eventually coagulate. Some agglomeration of particles may occur even in the presence of a suitable dispersant but when the dispersant type and concentration is optimised then such agglomeration should be at a relatively low level and the agglomerates may form only loosely so that they may be broken up and the particles redispersed by agitation.

The polymeric dispersant may include homopolymers or copolymers including polymers such as graft copolymers and star polymers.

Preferably, the polymeric dispersant has sufficiently acidic or basic functionality to substantially stabilise the colloidal suspension of said group VIIIB metal or metal compound.

By substantially stabilise is meant that the precipitation of the group VIIIB metal from the solution phase is substantially avoided.

Particularly preferred dispersants for this purpose include acidic or basic polymers including carboxylic acids, sulphonic acids, amines and amides such as polyacrylates or heterocycle, particularly nitrogen heterocycle, substituted polyvinyl polymers such as polyvinyl pyrrolidone or copolymers of the aforesaid.

Examples of such polymeric dispersants may be selected from polyvinylpyrrolidone, polyacrylamide, polyacrylonitrile, polyethylenimine, polyglycine, polyacrylic acid, polymethacrylic acid, poly(3-hydroxybutyricacid), poly-L-leucine, poly-L-methionine, poly-L-proline, poly-L-serine, poly-L-tyrosine, poly(vinylbenzenesulphonic acid) and poly(vinylsulphonic acid).

Preferably, the polymeric dispersant incorporates acidic or basic moieties either pendant or within the polymer backbone. Preferably, the acidic moieties have a dissociation constant ($pK_a$) of less than 6.0, more preferably, less than 5.0, most preferably less than 4.5. Preferably, the basic moieties have a base dissociation constant ($pK_b$) being of less than 6.0, more preferably less than 5.0 and most preferably less than 4.5, $pK_a$ and $pK_b$ being measured in dilute aqueous solution at 25° C.

Suitable polymeric dispersants, in addition to being soluble in the reaction medium at reaction conditions, contain at least one acidic or basic moiety, either within the polymer backbone or as a pendant group. We have found that polymers incorporating acid and amide moieties such as polyvinylpyrollidone (PVP) and polyacrylates such as polyacrylic acid (PAA) are particularly suitable. The molecular weight of the polymer which is suitable for use in the invention depends upon the nature of the reaction medium and the solubility of the polymer therein. We have found that normally the average molecular weight is less than 100,000. Preferably, the average molecular weight is in the range 1,000-200,000, more preferably, 5,000-100,000, most preferably, 10,000-40,000 e.g. Mw is preferably in the range 10,000-80,000, more preferably 20,000-60,000 when PVP is used and of the order of 1,000-10,000 in the case of PAA.

The effective concentration of the dispersant within the reaction medium should be determined for each reaction/catalyst system which is to be used.

The dispersed group VIIIB metal may be recovered from the liquid stream removed from the reactor e.g. by filtration and then either disposed of or processed for re-use as a catalyst or other applications. In a continuous process the liquid stream may be circulated through an external heat-exchanger and in such cases it may be convenient to locate filters for the palladium particles in these circulation apparatus.

Preferably, the polymer:metal mass ratio in g/g is between 1:1 and 1000:1, more preferably, between 1:1 and 400:1, most preferably, between 1:1 and 200:1. Preferably, the polymer:metal mass ratio in g/g is up to 1000, more preferably, up to 400, most preferably, up to 200.

Preparation of 1,2-bis-(di-(1,3,5,7-tetramethyl-6,9,10-trioxa-2-phospha-adamantylmethyl)) ferrocene 1,3,5,7-tetramethyl-2,4,8-trioxa-6-phospha-adamantane (obtained from Cytec, 14.0 g, 0.066 mol) was added to a solution of 1,2-bis(dimethylaminomethyl)ferrocene (Example 1, 10 g, 0.033 mol) in anhydrous acetic acid (100 ml) under nitrogen and the resulting mixture is stirred at 80° C. for 72 hours. The anhydrous acetic acid is removed in vacuo at approximately 70° C. to yield the crude title product as an orange/yellow solid. This is washed with hot methanol to give the product as a mixture of isomers as an orange solid. (12.0 g, 58%).

$^1$H NMR (250 MHz; CDCl$_3$): δ4.25-3.95 (8H, br, m); 3.46 (4H, br); 1.57-2.0 (8H, br, m); 1.43-1.23 (24H, br m).

$^{31}$P NMR (101 MHz; CDCl$_3$): δ−27.41 (br), −29.01 (s), −33.9 (br) ppm.

Elemental analysis: Found: C: 57.80%; H: 7.35%. Calculated: C: 57.87%; H: 7.40%.

Synthesis of 1.2-P,P'-di (2-phospha-1,3,5,7-tetramethyl-6,9,10-trioxatricyclo[3.3.1.1[3.7]decyl)-methylene-benzene Synthesis Step 1:

To a solution of 2-phospha-1,3,5,7-tetramethyl-6,9,10-trioxatricyclo[3.3.1.1{3.7}]decane hydride (H-PA) (13 g, 60 mmol) in tetrahydrofuran (40 ml) was added a 1 M solution of boron trihydride (73 mmol) in tetrahydrofuran over 5 min at 0° C. After 4 h stirring at room temperature (20° C.), the solvent was removed and the crude product was recrystallised from the minimum volume hot tetrahydrofuran (20 ml) and washed with hexane (2×5 ml) to afford 2-phospha-1,3,5,7-tetramethyl-6,9,10-trioxatricyclo[3.3.1.1 [3.7]]decane borane (H-PA.BH$_3$) as colourless crystals. Further product was obtained by recrystallisation of the filtrate from hot tetrahydrofuran (7 ml). The yield of H-PA.BH$_3$ was 86% based on H-PA.

Synthesis Step 2:

To a solution of H-PA.BH$_3$ (3.67 g, 16 mmol) in tetrahydrofuran (40 ml) was added hexyllithium (6.4 ml (2.5 M), 16 mmol) at −75° C. After stirring for 1 h, α,α'-dibromo-o-xylene (2.1 g, 8 mmol) in tetrahydrofuran (20 ml) was added at −75° C. and the reaction allowed to warm to room temperature. After 3 hours, diethylamine (3 ml, 28 mmol) was added and the reaction refluxed for 2 hours. After cooling, the solvent was removed and the crude product dissolved in toluene (60 ml) and washed with water (4×40 ml). The solvent was removed to afford 1,2-P,P$^1$-di(2-phospha-1,3,5,7-tetramethyl-6,9,10-trioxatricyclo[3.3.1.1{3.7}]decyl)-methylene-benzene (3.9 g, 91%) as a white solid (see thesis by Robert Pugh submitted to the University of Bristol in April 2000 for NMR characterization). The diphosphine may be further purified by recrystallisation from methanol.

Vinyl Acetate Carbonylation 1,2-bis(di-2{1,3,5-trimethyl-6,9,10-trioxa-adamantylphosphinomethyl})ferrocene (FePA) (Metal:Ligand:Acid ratio (M:L:A ratio)=1:1.25:2)

Standard conditions were as follows: In an oxygen free (<10 ppm O2) environment Pd(OAc)$_2$ (134.7 mg, 0.6 mmoles Pd) and 1,2-bis(2-phosphinomethyl-1,3,5-trimethyl-6,9,10-trioxa-adamantyl)ferrocene (492.3 mg, 0.75 mmoles) were weighed into a 500 ml round bottom flask. To this under a protective atmosphere of nitrogen 300 ml of degassed methanol was added, and the solution allowed to stir for one hour. Then methane sulphonic acid (77.9 ul, 1.2 mmoles,) was added and 50 ml of degassed vinyl acetate (VAM). This solution was added to an autoclave under vacuum, and heated to 60° C., when 10 bar of CO was added, and the solution allowed to react for 3 hours. The solution was then cooled, the pressure released, and the autoclave emptied. A GC sample was taken for analysis.

| Run | Ligand | Linear: Branched Ratio | % Conversion to Products | % Conversion of VAM to Products |
|---|---|---|---|---|
| 1 | FePA | 5.99 | 56.63 | 56.33 |
| 2 | FePA | 5.87 | 64.75 | 64.07 |
| 3 | FePA | 5.93 | 60.38 | 60.00 |

1,2-bis(di-2{1,3,5-trimethyl-6,9,10-trioxa-adamantylphosphinomethyl})benzene (XylyPA) (M:L:A ratio=1:1.25:2)

Standard conditions were as follows: In an oxygen free (<10 ppm O2) environment Pd(OAc)$_2$ (134.7 mg, 0.6 mmoles Pd) and 1,2-bis(2-phosphinomethyl-1,3,5-trimethyl-6,9,10-trioxa-adamantyl)benzene (411.4 mg, 0.75 mmoles) were weighed into a 500 ml round bottom flask. To this under a protective atmosphere of nitrogen 300 ml of degassed methanol was added, and the solution allowed to stir for one hour. Then methane sulphonic acid (77.9 ul, 1.2 mmoles,) was added and 50 ml of degassed vinyl acetate (VAM). This solution was added to an autoclave under vacuum, and heated to 60° C., when 10 bar of CO was added, and the solution allowed to react for 3 hours. The solution was then cooled the pressure released, and the autoclave emptied. A GC sample was taken for analysis.

| Run | Ligand | Linear: Branched Ratio | % Conversion to Products | % Conversion of VAM to Products |
|---|---|---|---|---|
| 1 | XylyPA | 6.16 | 62.07 | 61.83 |

After distillation of the products of the carbonylation, 2-acetoxy methyl propionate and 3-acetoxy methyl propionate were collected as different distillates.

Production of Lactate and 3-Hydroxy Esters

Preparation of 3 Hydroxymethylpropionate

To 25 g of 3 acetoxy methyl propionate (0.171 moles) was added 25 g MeOH (0.78 moles) containing 1% w/w methane sulphonic acid. The solution was stirred at 60 C for six hours before cooling to room temperature. The sample was analysed by GC, the peak corresponding to 3 acetoxy methylpropionate had completely disappeared and been replaced by a peak corresponding to 3 hydroxymethylpropionate.

Preparation of 2-Hydroxymethylpropionate

To 25 g of 2 acetoxy methylpropionate (0.171 moles) was added 25 g MeOH (0.78 moles) containing 1% w/w methane sulphonic acid. The solution was stirred at 60 C for six hours before cooling to room temperature. The sample was analysed by GC, the peak corresponding to 2 acetoxy methylpropionate had completely disappeared and been replaced by a peak corresponding to 2 hydroxymethylpropionate.

Preparation of 2 Hydroxy Propionic Acid (Lactic Acid)

To 25 g of 2 acetoxy methyl propionate (0.171 moles) was added 25 g MeOH. To this stirred solution was added 20 g sodium hydroxide (0.5 moles) dissolved in 20 ml of water. The solution was stirred for one hour at 50 C before cooling to room temperature. The pH of the solution was then adjusted to pH 3.0 by the slow addition of HCl and the sample stirred for 1 hour. The sample was analysed by GC, the peak corresponding to 2 acetoxy methyl propionate had completely disappeared and been replaced by a peak corresponding to 2 hydroxy propionic acid.

Preparation of 3 Hydroxy Propionic Acid

To 25 g of 3 acetoxy methyl propionate (0.171 moles) was added 25 g MeOH. To this stirred solution was added 20 g sodium hydroxide (0.5 moles) dissolved in 20 ml of water. The solution was stirred for one hour at 50 C before cooling to room temperature. The pH of the solution was then adjusted to pH 3.0 by the slow addition of HCl and the sample stirred for 1 hour. The sample was analysed by GC, the peak corresponding to 3 acetoxy methyl propionate had completely disappeared and been replaced by a peak corresponding to 3 hydroxy propionic acid.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A process for the alkoxycarbonylation of a vinyl ester to give predominantly linear product comprising reacting a vinyl ester with carbon monoxide in the presence of an alkanol and of a catalyst system, the catalyst system obtainable by combining:
   (a) a metal of Group VIII B or a compound thereof: and
   (b) a bidentate ligand of general formula (I)

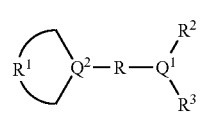

(I)

wherein:
   the bridging group R is defined as -A-(K,D)Ar(E,Z)—B— wherein:
   Ar is a bridging group comprising an optionally substituted aryl moiety to which the $Q^1$ and $Q^2$ atoms are linked on available adjacent carbon atoms;
   A and B each independently represent lower alkylene;
   K, D, E and Z are substituents of the aryl moiety (Ar) and each independently represent hydrogen, lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$, $C(O)SR^{27}$, or $-J-Q^3(X^5)X^6$ where J represents lower alkylene; or two adjacent groups selected from K, Z, D and E together with the carbon atoms of the aryl ring to which they are attached form a further phenyl ring, which is optionally substituted by one or more substituents selected from hydrogen, lower alkyl, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$ or $C(O)SR^{27}$ or, when Ar is a cyclopentadienyl group, Z may be represented by $-M(L_1)_n(L_2)_m$ and Z is connected via a metal ligand bond to the cyclopentadienyl group;
   $X^5$ represents $CR^{13}(R^{14})(R^{15})$, congressyl or adamantyl, $X^6$ represents $CR^{16}(R^{17})(R^{18})$, congressyl or adamantyl, or $X^5$ and $X^6$ together with $Q^3$ to which they are attached form an optionally substituted 2-$Q^3$-tricyclo[3.3.1.1.{3,7}] decyl group or derivative thereof in which one or more of the carbon atoms are replaced by heteroatoms;
   $R^1$ together with $Q^2$ to which it is attached form an optionally substituted 2-$Q^2$-tricyclo[3.3.1.1{3,7}]decyl group or derivative thereof in which one or more of the carbon atoms are replaced by heteroatoms;
   R2 and R3 independently represent univalent radicals containing up to 20 atoms or jointly form a bivalent radical of up to 20 atoms;
   Q1 and Q2 each independently represent phosphorus, arsenic or antimony.

2. A process according to claim 1, wherein $Q^2$ is phosphorus.

3. A process according to claim 1, wherein $R^2$ represents $CR^4(R^5)(R^6)$, congressyl or adamantyl, $R^3$ represents $CR^7(R^8)(R^9)$, congressyl or adamantyl, or $R^2$ and $R^3$ together with $Q^1$ to which they are attached form an optionally substituted 2-$Q^1$-tricyclo[3.3.1.1{3,7}]decyl group or derivative thereof, wherein $R^4$ to $R^9$ each independently represent lower alkyl or aryl.

4. A process according to claim 3, wherein the adamantyl group optionally comprises, besides hydrogen atoms, one or more substituents selected from lower alkyl, $-OR^{19}$, $-OC(O)R^{20}$, halo, nitro, $-C(O)R^{21}$, $-C(O)OR^{22}$, cyano, aryl, $-N(R^{23})R^{24}$, $-C(O)N(R^{25})R^{26}$, $-C(S)R^{27})R^{28}$, $-CF_3$, $-P(R^{56})R^{57}$, $-PO(R^{58})(R^{59})$, $-PO_3H_2$, $-PO(OR^{60})(OR^{61})$, or $-SO_3R^{62}$, wherein $R^{19}$, $R^{20}$, $R^{21}$, $R^{22}$, $R^{23}$, $R^{24}$, $R^{25}$, $R^{26}$, $R^{27}$, $R^{28}$, lower alkyl, cyano and aryl are as defined herein and $R^{56}$ to $R^{62}$ each independently represent hydrogen, lower alkyl, aryl or Het.

5. A process according to claim 1, wherein the 2-$Q^2$(or $Q^1$)-tricyclo[3.3.1.1.{3,7}]decyl group (referred to hereinafter as a 2-meta-adamantyl group for convenience wherein 2-meta-adamantyl is a reference to 2-arsa-adamantyl and/or 2-stiba-adamantyl and/or 2-phospha-adamantyl), optionally comprises, beside hydrogen atoms, one or more substituents selected from lower alkyl, $-OR^{19}$, $-OC(O)R^{20}$, halo, nitro, $-C(O)R^{21}$, $-C(O)OR^{22}$, cyano, aryl, $-N(R^{23})R^{24}$, $-C(O)N(R^{25})R^{26}$, $-C(S)(R^{27})R^{28}$, $-CF_3$, $-P(R^{56})R^{57}$, $-PO(R^{58})(R^{59})$, $-PO_3H_2$, $-PO(OR^{60})(OR^{61})$, or $-SO_3R^{62}$, wherein $R^{19}$, $R^{20}$, $R^{21}$, $R^{22}$, $R^{23}$, $R^{24}$, $R^{25}$, $R^{26}$, $R^{27}$, $R^{28}$, lower alkyl, cyano and aryl are as defined herein and $R^{56}$ to $R^{62}$ each independently represent hydrogen, lower alkyl, aryl or Het.

6. A process according to claim 5, wherein the 2-meta-adamantyl group includes additional heteroatoms, other than the 2-Q atom, in the 2-meta-adamantyl skeleton.

7. A process according to claim 1, wherein the 2-meta-adamantyl groups as defined herein include 2-phospha-1,3,5,7-tetramethyl-6,9,10-trioxadamantyl group, 2-phospha-1,3,5-trimethyl-6,9,10-trioxadamantyl group, 2-phospha-1,3,5,7-tetra(trifluoromethyl)-6,9,10-trioxadamantyl group, and 2-phospha-1,3,5-tri(trifluoromethyl)-6,9,10-trioxadamantyl group.

8. A process according to claim 1, wherein suitable Group VIIIB metals or a compound thereof which may be combined with a compound of formula I include cobalt, nickel, palladium, rhodium and platinum.

9. A process according to claim 1, wherein the ratio of linear:branched product from the alkoxycarbonylation process is greater than 1.5:1.

10. A process according to claim 1, wherein the bidentate ligands are selected from 1,2-bis(2-phosphinomethyl-1,3,5,7-tetramethyl-6,9,10-trioxa-adamantyl)ferrocene, 1,2-bis(2-phosphinomethyl-1,3,5,7-tetramethyl-6,9,10-trioxa-adamantyl)benzene, 1,2,3-tris(2-phosphinomethyl-1,3,5,7-tetramethyl-6,9,10-trioxa-adamantyl)ferrocene; 1-(2-phosphinomethyl-1,3,5,7-tetramethyl-6,9,10-trioxa-adamantyl)-2-(di-utylphosphinomethyl)benzene; 1-(2-phosphinomethyl-1,3,5,7-tetramethyl-6,9,10-trioxa-adamantyl)-2-(diadamantylphosphinomethyl)benzene; 1,2-bis(2-phosphinomethyl-1,3,5,7-tetramethyl-6,9,10-trioxa-adamantyl)naphthalene;
or the bidentate ligand is bonded to a suitable polymeric substrate via at least one of the bridging group, the linking group A or the linking group B.

11. The process according to claim 1, wherein the carbonylation is carried out at a temperature of between −10 to 150° C.

12. The process according to claim 1, wherein the carbonylation is carried out at a CO partial pressure of between $0.80 \times 10^5$ N.m$^{-2}$-$90 \times 10^5$ N.m$^{-2}$.

13. A process for the production of a 3-hydroxy propanoate ester or acid using the process according claim 1, followed by treatment of the linear (n) product of the alkoxycarbonylation.

14. A process for the production of a lactate ester or acid of formula III

(III)

comprising the steps of alkoxycarbonylating vinyl ester with carbon monoxide in the presence of an alkanol and a catalyst system, the catalyst system obtainable by combining:
 (a) a metal of Group VIII B or a compound thereof: and
 (b) a bidentate ligand of general formula (I) in accordance with claim 1
to produce a product comprising a branched (iso) product chemically treating the said branched (iso) product to produce the corresponding lactate or acid of formula III, wherein $R^{28}$ is selected from H, or a $C_1$-$C_{30}$ alkyl or aryl moiety which may be substituted or unsubstituted and either branched or linear.

15. A process for the production of a 3-hydroxy propanoate ester or acid according to claim 13, wherein the ester or acid is of formula (II)

(II)

wherein $R^{28}$ is selected from H, or a $C_1$-$C_{30}$ alkyl or aryl moiety which may be substituted or unsubstituted and either branched or linear.

16. A process according to claim 13, wherein the treatment step is carried out on the linear (n) product $CH_3C(O)OCH_2CH_2C(O)OR^{28}$, to produce the product of formula II, wherein $R^{28}$ is selected from H, or a $C_1$-$C_{30}$ alkyl or aryl moiety which may be substituted or unsubstituted and either branched or linear.

17. A process for the production of 3-hydroxy propanoate ester or acid of formula (II)

(II)

comprising the steps of
alkoxycarbonylating vinyl ester with carbon monoxide in the presence of an alkanol and a catalyst system, the catalyst system obtainable by combining:
 (a) a metal of Group VIII B or a compound thereof: and
 (b) a bidentate ligand of general formula (I) in accordance with claim 1
wherein $R^{28}$ is selected from H, or a $C_i$-$C_{30}$ alkyl or aryl moiety which may be substituted or unsubstituted and either branched or linear and carrying out a treatment step on the said linear (n) product $CH_3C(O)OCH_2CH_2C(O)OR^{28}$, to produce the 3-hydroxy propanoate ester or acid of formula (II).

18. A process according to claim 14, wherein the treatment step is carried out on the branched (iso) product, $CH_3CH(OC(O)CH_3)C(O)OR^{28}$, wherein $R^{28}$ is selected from H, or a $C_1$-$C_{30}$ alkyl or aryl moiety which may be substituted or unsubstituted and either branched or linear.

* * * * *